US008614370B2

(12) United States Patent
Andersen et al.

(10) Patent No.: US 8,614,370 B2
(45) Date of Patent: Dec. 24, 2013

(54) **NUCLEIC ACID SEQUENCES FROM *DIABROTICA VIRGIFERA VIRGIFERA* LECONTE AND USES THEREOF**

(75) Inventors: Scott E. Andersen, St. Louis, MO (US); Glenn R. Hicks, Castro Valley, CA (US); Joseph E. Huesing, Chesterfield, MO (US); Charles P. Romano, Chesterfield, MO (US); Clayton S. Vetsch, North Stonington, CT (US)

(73) Assignee: Monsanto Technology LLC, St. Louis, MO (US)

( * ) Notice: Subject to any disclaimer, the term of this patent is extended or adjusted under 35 U.S.C. 154(b) by 399 days.

(21) Appl. No.: 12/606,948

(22) Filed: Oct. 27, 2009

(65) Prior Publication Data
US 2011/0154545 A1   Jun. 23, 2011

Related U.S. Application Data

(62) Division of application No. 10/205,189, filed on Jul. 24, 2002, now Pat. No. 7,612,194.

(60) Provisional application No. 60/307,512, filed on Jul. 24, 2001.

(51) Int. Cl.
*C12N 15/82* (2006.01)
*C12N 15/87* (2006.01)
*A01H 1/00* (2006.01)
*C07H 21/04* (2006.01)

(52) U.S. Cl.
USPC ........... 800/285; 800/286; 800/279; 536/24.5

(58) Field of Classification Search
None
See application file for complete search history.

(56) References Cited

U.S. PATENT DOCUMENTS

| | | | |
|---|---|---|---|
| 4,948,734 A | 8/1990 | Edwards et al. ........... 435/252.5 |
| 5,107,065 A | 4/1992 | Shewmaker et al. ......... 800/298 |
| 5,231,020 A | 7/1993 | Jorgensen et al. ............ 800/281 |
| 5,283,184 A | 2/1994 | Jorgensen et al. ............ 800/285 |
| 5,629,469 A | 5/1997 | Deluca-Flaherty et al. .. 800/205 |
| 5,759,829 A | 6/1998 | Shewmaker et al. ......... 800/286 |
| 6,326,193 B1 | 12/2001 | Liu et al. ..................... 435/320.1 |
| 6,506,559 B1 | 1/2003 | Fire et al. ......................... 435/6 |
| 6,703,491 B1 | 3/2004 | Homburger et al. |
| 7,109,393 B2 | 9/2006 | Gutterson |
| 7,348,410 B2 | 3/2008 | Gaines et al. ................. 530/350 |
| 7,612,194 B2 | 11/2009 | Andersen et al. |
| 7,741,531 B2 | 6/2010 | Baltz et al. |
| 7,943,819 B2 | 5/2011 | Baum et al. |
| 8,404,927 B2 | 3/2013 | Allen et al. |
| 2002/0048814 A1 | 4/2002 | Oeller ........................... 435/455 |
| 2003/0061626 A1 | 3/2003 | Plaetinck et al. ................. 800/8 |
| 2003/0150017 A1 | 8/2003 | Mesa et al. ................... 800/279 |
| 2003/0175965 A1 | 9/2003 | Lowe et al. ................... 435/455 |
| 2004/0029283 A1 | 2/2004 | Fillatti ........................... 435/468 |
| 2006/0021087 A1 | 1/2006 | Baum et al. |
| 2006/0174380 A1 | 8/2006 | Carrington et al. ........... 800/285 |
| 2009/0307803 A1 | 12/2009 | Baum et al. |
| 2010/0192265 A1 | 7/2010 | Andersen et al. |
| 2012/0137387 A1 | 5/2012 | Baum et al. |
| 2012/0164205 A1 | 6/2012 | Baum et al. |

FOREIGN PATENT DOCUMENTS

| | | |
|---|---|---|
| CA | 2 094 658 A1 | 10/1993 |
| WO | WO 94/01550 | 1/1994 |
| WO | WO 98/05770 | 2/1998 |
| WO | WO 99/31253 | 6/1999 |
| WO | WO 99/36520 | 7/1999 |
| WO | WO 99/49029 | 9/1999 |
| WO | WO 99/53050 | 10/1999 |
| WO | WO 01/09301 A2 | 2/2001 |
| WO | WO 01/34815 A1 | 5/2001 |
| WO | WO 01/37654 | 5/2001 |
| WO | WO 02/46432 A2 | 6/2002 |
| WO | WO 03/004644 A1 | 1/2003 |
| WO | WO 03/076619 A1 | 9/2003 |
| WO | WO 2004/013169 | 2/2004 |
| WO | WO 2004/022771 A2 | 3/2004 |
| WO | WO 2005/019408 A2 | 3/2005 |
| WO | WO 2005/049841 | 6/2005 |
| WO | WO 2005/071091 A1 | 8/2005 |
| WO | WO 2005/110068 | 11/2005 |
| WO | WO 2006/045590 A2 | 5/2006 |
| WO | WO 2006/046148 | 5/2006 |
| WO | WO 2007/083193 A2 | 7/2007 |

OTHER PUBLICATIONS

Thomas et al. 2001, The Plant Journal 25(4):417-425.*
Beegle et al., "Invitation paper (CP Alexander Fund): history of *Bacillus thuringiensis* Berliner Research and Development," *Can. Entomol.*, 124:587-616, 1992.
Dalmay et al., "An RNA-dependent RNA polymerase gene in *Arabidopsis* is required for posttranscriptional gene silencing mediated by a transgene but not by a virus," *Cell*, 101:543-553, 2000.
Database EMBL, "*Drosophila melanogaster* RE24065 full length cDNA," Database accession No. AY071192, 2001.
Dow et al., "Molecular genetic analysis of V-ATPase function in *Drosophila melanogaster*," *J. Exp. Biol.*, 200(Pt. 2):237-245, 1997.
Dow, "The multifunctional *Drosophila melanogaster* V-ATPase is encoded by a multigene family," *J. Bioenerg. Biomembr.*, 31(1):75-83, 1999.
Elbashir et al., "Analysis of gene function in somatic mammalian cells using small interfering RNAs," *Methods*, 26(2):199-213, 2002.
Elbashir et al., "RNA interference is mediated by 21- and 22-nucleotide RNAs," *Genes Dev.*, 15:188-200, 2001.

(Continued)

*Primary Examiner* — Li Zheng
(74) *Attorney, Agent, or Firm* — Dentons US LLP; T. K. Ball, Esq.

(57) ABSTRACT

Expressed Sequence Tags (ESTs) isolated from the Western Corn Rootworm, *Diabrotica virgifera virgifera* LeConte, are disclosed. The invention encompasses nucleic acid molecules that encode *D. v. virgifera* protein homologs and fragments thereof. In addition, antibodies capable of binding the proteins are encompassed by the present invention. The disclosed ESTs have particular utility in isolating genes and promoters, identifying and mapping the genes involved in developmental and metabolic pathways, and determining gene function. The ESTs provide a unique molecular tool for the targeting and isolation of novel genes for plant protection and improvement. The invention also relates to methods of using the disclosed nucleic acid molecules, proteins, fragments of proteins, and antibodies, for example, for gene identification and analysis, and preparation of constructs.

14 Claims, No Drawings

(56) References Cited

OTHER PUBLICATIONS

Feitelson et al., "*Bacillus thuringiensis*: insects and beyond," *Bio/Technology*, 10:271-275, 1992.
Feitelson, "The *Bacillus thuringiensis* family tree", In: Advanced Engineered Pesticides, Kim Ed., Marcel Dekker, Inc., New York, pp. 63-71, 1993.
GenBank Accession No. AF008922, dated Jun. 17, 1997.
GenBank Accession No. L09234, Jun. 12, 1993.
GenPept Accession No. NP_001682, May 10, 2002.
Gill et al., "Isolation of the V-ATPase A and c subunit cDNAs from mosquito midgut and malpighian tubules," *Archives of Insect Biochemistry and Physiology*, 37-80-90, 1998.
Gill et al., "The mode of action of *Bacillus thuringiensis* endotoxins," *Annu. Rev. Entomol.*, 37:615-636, 1992.
Hamilton et al., "A species of small antisense RNA in post-transcriptional gene silencing in plants," *Science*, 286(5441):950-952, 1999.
Hofmann et al., "Specificity of *B. thuringiensis* delta-endotoxins is correlated with the presence of high-affinity binding sites in the brush border membrane of target insect midguts," *Proc. Natl. Acad. Sci. USA*, 85:7844-7848, 1988.
Kennerdell et al., "Heritable gene silencing in *Drosophila* using double-stranded RNA," *Nat. Biotechnol.*, 18:896-898, 2000.
Kennerdell et al., "Use of dsRNA-mediated genetic interference to demonstrate that frizzled and frizzled 2 act in the wingless pathway," *Cell*, 95:1017-1026, 1998.
Mourrain et al., "*Arabidopsis* SGS2 and SGS3 genes are required for posttranscriptional gene silencing and natural virus resistance," *Cell*, 101:533, 2000.
NCBI Accession No. AW671389, dated Jul. 19, 2000.
New England Biolabs Catalog, 1996/1997, p. 111, undated.
Peragine et al., "SGS3 and SGS2/SDE1/RDR6 are required for juvenile development and the production of trans-acting siRNAs in *Arabidopsis*," *Genes Dev.*, 18(19):2368-2379, 2004.
Rajagopal et al., "Silencing of midgut aminopeptidase N of *Spodoptera litura* by double-stranded RNA establishes its role as *Bacillus thuringiensis* toxin receptor," *J. Biol. Chem.*, 277:46849-46851, 2002.
Tabara et al., "RNAi in *C. elegans*: soaking in the genome sequence," *Science*, 282(5388):430-431, 1998.
Tabashnik, "Evaluation of synergism among *Bacillus thuringiensis* toxins," *Appl. Environ. Microbiol.*, 58(10):3343-3346, 1992.
Van Rie et al., "Receptors on the brush border membrane of the insect midgut as determinants of the specificity of *Bacillus thuringiensis* delta-endotoxins," *Appl. Environ. Microbiol.*, 56(5):1378-1385, 1990.
Van Rie et al., "Specificity of *Bacillus thuringiensis* δ-endotoxins," *Eur. J. Biochem.*, 186:239-247, 1989.
Vazquez et al., "Endogenous trans-acting siRNAs regulate the accumulation of *Arabidopsis* mRNAs," *Mol. Cell*, 16(1):69-79, 2004.
Yadav et al., "Host-generated double stranded RNA induces RNAi in plant-parasitic nematodes and protects the host from infection," *Molec. Biochem. Parasitol.*, 148(2):219-222, 2006.
Björklund et al, "Identification of pathways regulation cell size and cell progression by RNA1," (*Nature*, 23:439(7079)1009-13, 2006.
Fire, "RNA triggered gene silencing," *Trends in Genetic*, 15(9):358-363, 1999.
GenBank Accession No. AM048926, dated Jul. 16, 2005.
GenBank Accession No. AY166605, dated Dec. 10, 2008.
GenPept Accession No. Q4GXU7, dated Nov. 28, 2006.
Graf et al., "Cloning and sequencing of cDNA encoding the putative insect plasma membrane V-ATPase subunit A," *FEBS Letters*, 300(2):119-122, 1992.
Lamberton et al., "Varying the nucleic acid composition of siRNA molecules dramatically varies the duration and degree of gene silencing," *Mol. Biotech.*, 24(2):111-119, 2003.
Manoharan, "Oligonucleotide conjugates as potential antisense drugs with improved uptake, biodistribution, targeted delivery, and mechanism of action," *Antisens & Nucliec Acid Drug Development*, 12:103-128, 2002.
Montgomery et al., "Double-stranded RNA as a mediator in sequence-specific genetic silencing and co-suppression," *Trends in Genetics*, 14(7):255-258, 1998.
Peter et al., "β-Cop is essential for Transport of Protein from the Endoiplasmic Reticulum to the Golgi in Vitro," *J Cell Biol* 122(6):1155-67, 1993.
Soares et al., "Capillary feeding of specific dsRNA induces silencing of ISAC gene in nymphal ixodes scapularis ticks," *Insect Molecular Biol.*, 14(4):443-452, 2005.
Timmons et al., "Specific interference by ingested dsRNA," *Nature*, 395(6705):854, 1998.
Titarenko et al., "cDNA cloning biochemical characterization and inhibition by plant inhibitors of the alpha-amylases of the Western corn rootworm, *Diabrotica virgifera virgifera*," *Insect Biochem. and Mol. Biol.*, 30(10):979-990, 2000.
U.S. Appl. No. 13/783,125, filed Mar. 1, 2013, Baum et al.
U.S. Appl. No. 13/855,328, filed Apr. 2, 2013, Baum et al.
Preliminary Amendment in U.S. Appl. No. 13/855,328 dated Apr. 2, 2013.
Preliminary Amendment in U.S. Appl. No. 13/783,125 dated Mar. 1, 2013.

\* cited by examiner

NUCLEIC ACID SEQUENCES FROM *DIABROTICA VIRGIFERA VIRGIFERA* LECONTE AND USES THEREOF

This application is a divisional of U.S. patent application Ser. No. 10/205,189, filed Jul. 24, 2002, now U.S. Pat. No. 7,612,194, the disclosure of which is incorporated herein by reference in its entirety, which application claims the benefit of priority of U.S. Provisional Patent Application No. 60/307,512, filed Jul. 24, 2001.

The Sequence Listing, which is a part of the present disclosure, includes a computer readable 6,404 KB file entitled "MONS192USD1US_ST25.txt" comprising nucleotide and/or amino acid sequences of the present invention submitted via EFS-Web. The subject matter of the Sequence Listing is incorporated herein by reference in its entirety.

FIELD OF THE INVENTION

The present invention is in the field of molecular biology; more particularly, the present invention relates to nucleic acid sequences from the western corn rootworm, *Diabrotica virgifera virgifera* LeConte. The invention encompasses nucleic acid molecules that encode proteins and fragments of proteins. In addition, proteins and fragments of proteins so encoded and antibodies capable of binding the proteins are encompassed by the present invention. The invention also relates to methods of using the disclosed nucleic acid molecules, proteins, fragments of proteins, and antibodies, for example, for gene identification and analysis, and preparation of constructs.

BACKGROUND OF THE INVENTION

The western corn rootworm (WCRW), *Diabrotica virgifera virgifera* LeConte, is a major pest of corn in the United States. The western corn rootworm overwinters in the egg stage in fields where corn was grown the previous season. The eggs hatch from late May through June. Thereafter, the larvae pass through 3 larval stages, or instars, feeding upon the corn root system. Following completion of larval development, the larvae transform into pupae, which are white and immobile. Adults of western corn rootworms begin to emerge in early July and continue to emerge from the pupae stage into August. Adult beetles feed on the corn foliage and silk. Female beetles lay the vast majority of their eggs in the soil of cornfields during August and early September. Western corn rootworm larvae can survive only on corn and a few other species of Poaceae (Branson and Ortman, *J. Econ. Entomol.* 60: 201-203 (1967); Branson and Ortman, *J. Econ. Entomol.* 60: 201-203 (1967)). Larval root feeding decreases plant vigor by reducing the water and nutrients supplied to the developing corn plants. Extensive root damage weakens the root system and makes the plants more susceptible to lodging (plants lean over or elbow), which eventually reduces corn yield and often results in death of the plant. Lodged plants are difficult to harvest resulting in further yield losses. The western corn rootworm adults feed upon corn leaves, which can slow plant growth and, on rare occasions, kill plants of some corn varieties. The western corn rootworm cause economic losses throughout the Midwest and in certain eastern and northeastern states where corn is produced.

Control of corn rootworms has been partially addressed by crop rotation. However, economic demands on the utilization of farmland restrict the use of crop rotation. In addition, the spread of at least one strain of rootworm has been documented in which female oviposition occurs in soybean fields, which further complicates crop rotation strategies. Therefore, chemical insecticides are relied upon most heavily to guarantee the desired level of control. Over $250 million worth of insecticides are applied annually to control corn rootworms alone in the United States. Even with insecticide use, rootworms still can cause over $750 million worth of crop damage each year. The use of chemical insecticides to control corn rootworm has several drawbacks. Continual use of insecticides has allowed resistant insects to evolve. Situations such as extremely high populations of larvae, heavy rains, and improper calibration of insecticide application equipment can result in poor control. Chemical insecticides used for corn rootworm control often raises environmental concerns such as contamination of soil and of both surface and underground water supplies, because many of them are toxic to humans, wildlife and other nontarget species. As a result, much research has been concentrated in the area of biopesticides.

The advantage of using biopesticides is that they are generally less harmful to non-target organisms and the environment as a whole compared to chemical pesticides. The most widely used biopesticide is *Bacillus thuringiensis* (Bt), which is a spore-forming gram-positive bacterium. During sporulation, *B. thuringiensis* produces proteinaceous inclusions which are composed of proteins known as insecticidal crystal proteins (ICPs), Cry proteins, or delta-endotoxins. These proteins are toxic to a variety of insect species including orders Lepidoptera, Coleoptera, Diptera, Hemoptera, Hymenoptera, Orthoptera, and Mallophaga (Beegle and Yamamoto, *Can. Entomol.* 124:587-616; Feitelson, Advanced Engineered Pesticides (L. Kim, ed.), Marcel Dekker, Inc., New York (1993), pp. 63-71; Feitelson, et al., *Bio/Technology* 10:271-275; U.S. Pat. No. 4,948,734 (1990)). Due to their high specificity for particular insect pests and their safety for man and the environment, ICPs have been used as biopesticides for the last three decades.

It has been established that the Bt toxins function in the brush border of the insect midgut epithelial cells as described by Gill et al., *Annu. Rev. Entomol.* 37: 615 (1992). Specific binding of Bt toxins to midgut brush border membrane vesicles has been reported by Hofmann et al., *Proc. Natl. Acad. Sci. USA* 85: 7844 (1988); Van Rie et al., *Eur. J. Biochem.* 186: 239 (1989); and Van Rie, J. et al. *Appl. Environ. Microbiol.* 56: 1378 (1990). It is believed that the specificity of Bt toxins is determined by their specific interaction with receptors in insects' guts. It is advantageous to identify and/or isolate receptors as targets for insecticidal peptides in the guts of western corn rootworms. It is further advantageous to develop target-based screens to produce insecticidal peptides.

A cDNA (or complementary DNA) library, which is constructed from mRNA purified from WCRW intestine, can be one valuable source for isolating receptor protein genes. Construction of cDNA libraries is well-known in the art and a number of cloning strategies exist Random clones from a cDNA library can be sequenced from both 3' and 5' ends to generate expressed sequence tags (ESTs), which can represent copies of up to the full length transcript (McCombie, et al., *Nature Genetics,* 1:124-130 (1992); Kurata, et al., *Nature Genetics,* 8: 365-372 (1994); Okubo, et al., *Nature Genetics,* 2: 173-179 (1992)). Typically, only single run sequence data is obtained from the cDNA library (Adams, et al., *Science* 252:1651-1656 (1991)). Automated single run sequencing typically results in an approximately 2-3% error or base ambiguity rate. (Boguski, et al., *Nature Genetics,* 4:332-333 (1993)). Between 150-450 nucleotides of sequence information is usually generated as this is the length of sequence information that is routinely and reliably produced using single run sequence data.

ESTs have been found to be useful for similarity searches and mapping (Adams, et al., *Science* 252:1651-1656 (1991)). Sequence comparisons and similarity analysis would allow the identification of receptors for insecticidal peptides and then full-length cDNA constructs can be obtained using several methods (Land, et al., *Nucleic Acids Res.* 9:2251-2266 (1981); Okayama and Berg, *Mol. Cell. Biol.* 2:161-170 (1982); Coleclough, et al., *Gene* 34:305-314 (1985); Krawinkel, et al., *Nucleic Acids Res.* 14:1913 (1986); Han, et al., *Nucleic Acids Res.* 15:6304 (1987)).

SUMMARY OF THE INVENTION

The present invention provides a substantially purified nucleic acid molecule having a nucleotide sequence which is or is complementary to a sequence selected from the group consisting of SEQ ID NO: 1 through SEQ ID NO: 9112.

The present invention also provides a substantially purified nucleic acid molecule, the nucleic acid molecule capable of specifically hybridizing to a second nucleic acid molecule having a nucleotide sequence which is or is complementary to a sequence selected from the group consisting of SEQ ID NO: 1 through SEQ ID NO: 9112.

The present invention further provides a substantially purified protein, peptide, or fragment thereof encoded by a nucleotide sequence which is or is complementary to a sequence selected from the group consisting of SEQ ID NO: 1 through SEQ ID NO:9112.

The present invention also provides a substantially purified nucleic acid molecule encoding a *D. v. virgifera* protein homologue or fragment thereof, wherein the nucleic acid molecules comprises a nucleotide sequence selected from the group consisting of SEQ ID NO: 1 through SEQ ID NO: 9112.

The present invention also provides a substantially purified nucleic acid molecule encoding a protein or fragment thereof, wherein the protein or fragment thereof is selected from the group consisting of *D. v. virgifera* proteins or fragments thereof from Table 1.

The present invention also provides a substantially purified protein or fragment thereof encoded by a nucleotide sequence selected from the group that encodes a *D. v. virgifera* protein or fragment thereof from Table 1.

The present invention also provides a substantially purified nucleic acid molecule encoding a *D. v. virgifera* receptor or fragment thereof for a protein toxic to *D. v. virgifera*, wherein the nucleic acid molecules comprise a nucleotide sequence selected from the group consisting of SEQ ID NO: 1 through SEQ ID NO: 9112.

The present invention also provides a substantially purified nucleic acid molecule encoding a *D. v. virgifera* receptor or fragment thereof for a protein toxic to *D. v. virgifera*, wherein the nucleic acid molecules comprise a nucleotide sequence selected from the group consisting of SEQ ID NO: 1 through SEQ ID NO: 9112 and wherein said protein is isolated from bacteria, fungi, plants and animals or produced by *B. thuringiensis, Photorhabdus*, and *Xenorhabdus*.

The present invention also provides a substantially purified receptor or fragment thereof encoded by a nucleotide sequence selected from the group that encodes a *D. v. virgifera* receptor or fragment thereof from Table 1.

The present invention also provides a substantially purified protein or fragment thereof encoded by a first nucleic acid molecule which specifically hybridizes to a second nucleic acid molecule, the second nucleic acid molecule selected from the group of complements of SEQ ID NO: 1 through SEQ ID NO: 9112.

The present invention also provides a transformed cell having a nucleic acid molecule which comprises: (A) an exogenous promoter region which functions in the cell to cause the production of a mRNA molecule; which is operably linked to (B) a structural nucleic acid molecule, wherein the structural nucleic acid molecule comprises a nucleotide sequence which is or is complementary to a sequence selected from the group consisting of SEQ ID NO:1 through SEQ ID NO:9112; which is operably linked to (C) a 3' non-translated sequence that functions in said cell to cause termination of transcription.

The present invention also provides a transformed cell having a nucleic acid molecule which comprises: (A) an exogenous promoter region which functions in the cell to cause the production of a mRNA molecule; which is operably linked to (B) a structural nucleic acid molecule, wherein the structural nucleic acid molecule encodes a receptor or fragment thereof which binds a protein toxic to *D. v. virgifera* and comprises a nucleotide sequence which is or is complementary to a sequence selected from the group consisting of SEQ ID NO:1 through SEQ ID NO:9112; which is operably linked to (C) a 3' non-translated sequence that functions in said cell to cause termination of transcription.

The present invention also provides a transformed cell having a nucleic acid molecule which comprises: (A) an exogenous promoter region which functions in the cell to cause the production of a mRNA molecule; which is operably linked to (B) a structural nucleic acid molecule, wherein the structural nucleic acid molecule encode a receptor or fragment thereof which binds a toxin and comprises a nucleotide sequence which is or is complementary to a sequence selected from the group consisting of SEQ ID NO:1 through SEQ ID NO:9112, wherein said receptor or fragment thereof is disposed at the surface of said cell; which is operably linked to (C) a 3' non-translated sequence that functions in said cell to cause termination of transcription.

The present invention also provides a plant cell, a mammalian cell, a bacterial cell, an insect cell, a fungal cell and an algal cell transformed with a nucleic acid molecule of the present invention.

The present invention also provides a method for identifying a candidate protein toxic to *D. v. virgifera* comprising: (a) culturing cells transformed with a nucleic acid molecule of the present invention; (b) recovering said cells having a receptor or fragment thereof disposed at their surface, wherein said receptor or fragment thereof binds a protein toxic to *D. v. virgifera*; (c) contacting said cells with said candidate protein; and (d) determining effects of said candidate protein on metabolism or morphology of said cells, wherein said determination is predictive of cytotoxic property of said candidate protein.

The present invention also provides a computer readable medium having recorded thereon one or more of the nucleotide sequences depicted in SEQ ID NO:1 through SEQ ID NO: 9112 or complements thereof.

DETAILED DESCRIPTION OF THE INVENTION

Agents of the Invention (a) Nucleic Acid Molecules

Agents of the present invention include substantially purified (or isolated) nucleic acid molecules and more specifically EST nucleic acid molecules or nucleic acid fragment molecules thereof. EST nucleic acid molecules may encode significant portion(s) of, or indeed most of, the EST nucleic acid molecule. Alternatively, the fragments may comprise smaller oligonucleotides (having from about 15 to about 250 nucleotide residues, and more preferably, about 15 to about 30 nucleotide residues).

A subset of the nucleic acid molecules of the present invention includes nucleic acid molecules that are marker molecules. Another subset of the nucleic acid molecules of the present invention include nucleic acid molecules that encode a protein or fragment thereof. Another subset of the nucleic acid molecules of the present invention are EST molecules.

In a preferred embodiment the nucleic acid molecules of the present invention are derived from leaf beetles belonging to the genus *Diabrotica* (Coleoptera:Chrysomelidae) and in an even more preferred embodiment the nucleic acid molecules of the present invention are derived from species in the *virgifera* group. In a particularly preferred embodiment the nucleic acid molecules of the present invention are derived from *Diabrotica virgifera virgifera* LeConte.

The term "nucleic acid molecule" or "nucleic acid" refers to a single or double-stranded polymer of deoxyribonucleotide or ribonucleotide bases read from the 5' to the 3' end. Nucleic acid molecules may also optionally contain synthetic, non-natural or altered nucleotide bases that permit correct read through by a polymerase and do not alter expression of a polypeptide encoded by that nucleic acid molecule.

As used herein, an agent, be it a naturally occurring molecule or otherwise may be "substantially purified" or "isolated", if desired, referring to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

As used herein "a substantially purified nucleic acid" or "an isolated nucleic acid" refers to a nucleic acid that is no longer accompanied by some of materials with which it is associated in its natural state or to a nucleic acid the structure of which is not identical to that of any of naturally occurring nucleic acid. Examples of a substantially purified nucleic acid include: (1) DNAs which have the sequence of part of a naturally occurring genomic DNA molecules but are not flanked by two coding sequences that flank that part of the molecule in the genome of the organism in which it naturally occurs; (2) a nucleic acid incorporated into a vector or into the genomic DNA of a prokaryote or eukaryote in a manner such that the resulting molecule is not identical to any naturally occurring vector or genomic DNA; (3) a separate molecule such as a cDNA, a genomic fragment, a fragment produced by polymerase chain reaction (PCR), or a restriction fragment; (4) recombinant DNAs; and (5) synthetic DNAs. A substantially purified nucleic acid may also be comprised of one or more segments of cDNA, genomic DNA or synthetic DNA.

It is also contemplated by the inventors that the substantially purified (or isolated) nucleic acids of the present invention also include known types of modifications, for example, labels which are known in the art, methylation, "caps", substitution of one or more of the naturally occurring nucleotides with an analog. Other known modifications include internucleotide modifications, for example, those with uncharged linkages (methyl phosphonates, phosphotriesters, phosphoamidates, carbamates, etc.) and with charged linkages (phosphorothioates, phosphorodithioates, etc.), those containing pendant moieties, such as, proteins (including nucleases, toxins, antibodies, signal peptides, poly-L-lysine, etc.), those with intercalators (acridine, psoralen, etc.), those containing chelators (metals, radioactive metals, boron, oxidative metals, etc.), those containing alkylators, and those with modified linkages.

It is understood that the agents of the present invention may be labeled with reagents that facilitate detection of the agent (e.g. fluorescent labels (Prober, et al., *Science* 238:336-340 (1987), Albarella et al., EP 144914), chemical labels (Sheldon et al., U.S. Pat. No. 4,582,789; Albarella et al., U.S. Pat. No. 4,563,417), modified bases (Miyoshi et al., EP 119448).

The term "nucleotide sequence" or "nucleic acid sequence" refers to both the sense and antisense strands of a nucleic acid as either individual single strands or in the duplex. It includes, but is not limited to, self-replicating plasmids, chromosomal sequences, and infectious polymers of DNA or RNA.

A "coding sequence", "structural nucleotide sequence" or "structural nucleic acid molecule" is a nucleotide sequence which is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, genomic DNA, cDNA, and recombinant nucleotide sequences.

The term "recombinant DNAs" refers to DNAs that contains a genetically engineered modification through manipulation via mutagenesis, restriction enzymes, and the like.

The term "synthetic DNAs" refers to DNAs assembled from oligonucleotide building blocks that are chemically synthesized using procedures known to those skilled in the art. These building blocks are ligated and annealed to form DNA segments which are then enzymatically assembled to construct the entire DNA. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines.

The agents of the present invention will preferably be "biologically active" with respect to either a structural attribute, such as the capacity of a nucleic acid to hybridize to another nucleic acid molecule, or the ability of a protein to be bound by antibody (or to compete with another molecule for such binding). Alternatively, such an attribute may be catalytic, and thus involve the capacity of the agent to mediate a chemical reaction or response.

It is further understood, that the present invention provides bacterial, insect, mammalian, viral, microbial, and plant cells comprising the agents of the present invention.

EST nucleic acid molecules or fragment EST nucleic acid molecules or other nucleic acid molecules of the present invention are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook, et al., In: *Molecular Cloning, A Laboratory Manual, 2nd Edition, Cold Spring Harbor Press*, Cold Spring Harbor, N.Y. (1989), and by Haymes, et al. In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. Thus, in order for an EST nucleic acid molecule or fragment EST nucleic acid molecule to serve as a primer or probe it need only be sufficiently complementary in sequence to be able to form a stable double-stranded structure under the particular solvent and salt concentrations employed.

Appropriate stringency conditions which promote DNA hybridization are, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to one or more of the nucleic acid molecules set forth in SEQ ID NO: 1 through SEQ ID NO: 9112 or complements thereof under moderately stringent conditions, for example at about 2.0×SSC and about 65° C.

In a particularly preferred embodiment, a nucleic acid of the present invention will include those nucleic acid molecules that specifically hybridize to one or more of the nucleic acid molecules set forth in SEQ ID NO:1 through SEQ ID NO: 9112 or complements thereof under high stringency conditions.

In one aspect of the present invention, the nucleic acid molecules of the present invention have one or more of the nucleotide sequences set forth in SEQ ID NO: 1 through to SEQ ID NO:9112 or complements thereof. In another aspect of the present invention, one or more of the nucleic acid molecules of the present invention share between 100% and 90% sequence identity with one or more of the nucleotide sequences set forth in SEQ ID NO: 1 through to SEQ ID NO:9112 or complements thereof. In a further aspect of the present invention, one or more of the nucleic acid molecules of the present invention share between 100% and 95% sequence identity with one or more of the nucleotide sequences set forth in SEQ ID NO: 1 through to SEQ ID NO:9112 or complements thereof. In a more preferred aspect of the present invention, one or more of the nucleic acid molecules of the present invention share between 100% and 98% sequence identity with one or more of the nucleotide sequences set forth in SEQ ID NO: 1 through to SEQ ID NO:9112 or complements thereof. In an even more preferred aspect of the present invention, one or more of the nucleic acid molecules of the present invention share between 100% and 99% sequence identity with one or more of the sequences set forth in SEQ ID NO: 1 through to SEQ ID NO:9112 or complements thereof. In a further, even more preferred aspect of the present invention, one or more of the nucleic acid molecules of the present invention exhibit 100% sequence identity with one or more nucleic acid molecules present within the cDNA libraries designated LIB149, LIB150, LIB3026, and LIB3373 (Monsanto Company, St. Louis, Mo., United States of America).

"Percentage of sequence identity" is determined by comparing two optimally aligned sequences over a comparison window, wherein the portion of the nucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Polypeptides which are "substantially similar" share sequences as noted above except that residue positions which are not identical may differ by conservative amino acid changes. Conservative amino acid substitutions refer to the interchangeability of residues having similar side chains. "Conservative amino acid substitutions" refer to substitutions of one or more amino acids in a native amino acid sequence with another amino acid(s) having similar side chains, resulting in a silent change. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine, valine-isoleucine, phenylalanine-tyrosine, lysine-arginine, alanine-valine, aspartic acid-glutamic acid, and asparagine-glutamine.

Optimal alignment of sequences for comparison can use any means to analyze sequence identity (homology) known in the art, e.g., by the progressive alignment method of termed "PILEUP" (Morrison, Mol. Biol. Evol. 14:428-441 (1997), as an example of the use of PILEUP); by the local homology algorithm of Smith & Waterman (Adv. Appl. Math. 2: 482 (1981)); by the homology alignment algorithm of Needleman & Wunsch (J. Mol. Biol. 48:443 (1970)); by the search for similarity method of Pearson (Proc. Natl. Acad. Sci. USA 85: 2444 (1988)); by computerized implementations of these algorithms (e.g., GAP, BESTFIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by, e.g., Higgins, Gene 73: 237-244 (1988); Corpet, Nucleic Acids Res. 16:10881-10890 (1988); Huang, Computer Applications in the Biosciences 8:155-165 (1992); and Pearson, Methods in Mol. Biol. 24:307-331 (1994); Pfam (Sonnhammer, Nucleic Acids Res. 26:322-325 (1998); TreeAlign (Hein, Methods Mol. Biol. 25:349-364 (1994); MEG-ALIGN, and SAM sequence alignment computer programs; or, by manual visual inspection.

Another example of algorithm that is suitable for determining sequence similarity is the BLAST algorithm, which is described in Altschul et al, J. Mol. Biol. 215: 403-410 (1990). Software for performing BLAST analyses is publicly available through the National Center for Biotechnology Information, www.ncbi.nlm.nih.gov/; see also Zhang, Genome Res. 7:649-656 (1997) for the "PowerBLAST" variation. This algorithm involves first identifying high scoring sequence pairs (HSPs) by identifying short words of length W in the query sequence that either match or satisfy some positive valued threshold score T when aligned with a word of the same length in a database sequence. T is referred to as the neighborhood word score threshold (Altschul et al, J. Mol. Biol. 215: 403-410 (1990)). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a wordlength (W) of 11, the BLOSUM62 scoring matrix (see Henikoff, Proc. Natl. Acad. Sci. USA 89:10915-10919 (1992)) alignments (B) of 50, expectation (E) of 10, M=5, N=−4, and a comparison of both strands. The term BLAST refers to the BLAST algorithm which performs a statistical analysis of the similarity between two sequences; see, e.g., Karlin, Proc. Natl. Acad. Sci. USA 90:5873-5787 (1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

In a preferred embodiment of the present invention, a nucleic acid molecule of the present invention encodes the homologue of a known protein. Table 1 sets forth a list of nucleic acid molecules that encode *D. v. virgifera* proteins or fragments thereof which are homologues of known proteins In a preferred embodiment of the present invention, a *D. v. virgifera* protein or fragment thereof of the present invention is a homologue of another insect protein. In another preferred embodiment of the present invention, a *D. v. virgifera* protein or fragment thereof of the present invention is a homologue of a fungal protein. In another preferred embodiment of the present invention, a *D. v. virgifera* protein or fragment thereof of the present invention is a homologue of a mammalian protein. In another preferred embodiment of the present invention, a *D. v. virgifera* protein or fragment thereof of the present invention is a homologue of a bacterial protein. In another preferred embodiment of the present invention, a *D. v. virgifera* protein or fragment thereof of the present invention is a homologue of an algal protein. In another preferred embodiment of the present invention, a *D. v. virgifera* protein or fragment thereof of the present invention is a homologue of a plant protein.

In a preferred embodiment of the present invention, the nucleic molecule of the present invention encodes a *D. v. virgifera* protein or fragment thereof where a *D. v. virgifera* protein or fragment thereof exhibits a BLAST probability score of greater than 1E-12, preferably a BLAST probability score of between about 1E-30 and about 1E-12, even more preferably a BLAST probability score of greater than 1E-30 with its homologue.

In another preferred embodiment of the present invention, the nucleic acid molecule encoding a *D. v. virgifera* protein or fragment thereof exhibits a percent identity with its homologue of between about 25% and about 40%, more preferably of between about 40% and about 70%, even more preferably of between about 70% and about 90% and even more preferably between about 90% and 99%. In another preferred embodiment, of the present invention, a *D. v. virgifera* protein or fragment thereof exhibits a percent identity with its homologue of 100%.

In a preferred embodiment of the present invention, the nucleic molecule of the present invention encodes a *D. v. virgifera* protein or fragment thereof where the *D. v. virgifera* protein exhibits a BLAST score of greater than 120, preferably a BLAST score of between about 1450 and about 120, even more preferably a BLAST score of greater than 1450 with its homologue.

The degeneracy of the genetic code, which allows different nucleotide sequences to code for the same protein or peptide, is known in the literature. (U.S. Pat. No. 4,757,006).

In an aspect of the present invention, one or more of the nucleic acid molecules of the present invention differ in nucleotide sequence from those encoding a *D. v. virgifera* protein or fragment thereof in SEQ ID NO: 1 through SEQ ID NO: 9112 due to the degeneracy in the genetic code in that they encode the same protein but differ in nucleotide sequence.

In another further aspect of the present invention, one or more of the nucleic acid molecules of the present invention differ in nucleotide sequence from those encoding a *D. v. virgifera* protein or fragment thereof in SEQ ID NO: 1 through SEQ ID NO: 9112 due to fact that the different nucleotide sequence encodes a protein having one or more conservative amino acid changes. It is understood that codons capable of coding for such conservative amino acid substitutions are known in the art.

It is well known in the art that one or more amino acids in a native sequence can be substituted with another amino acid(s), the charge and polarity of which are similar to that of the native amino acid, i.e., a conservative amino acid substitution, resulting in a silent change. Biologically functional equivalents of the proteins or fragments thereof of the present invention can have 10 or fewer conservative amino acid changes, more preferably seven or fewer conservative amino acid changes, and most preferably five or fewer conservative amino acid changes. The encoding nucleotide sequence will thus have corresponding base substitutions, permitting it to encode biologically functional equivalent forms of the proteins or fragments of the present invention.

It is understood that certain amino acids may be substituted for other amino acids in a protein structure without appreciable loss of interactive binding capacity with structures such as, for example, antigen-binding regions of antibodies or binding sites on substrate molecules. Because it is the interactive capacity and nature of a protein that defines that protein's biological functional activity, certain amino acid sequence substitutions can be made in a protein sequence and, of course, its underlying DNA coding sequence and, nevertheless, obtain a protein with like or superior properties. It is thus contemplated by the inventors that various changes may be made in the amino acid sequences of the proteins or fragments of the present invention, or corresponding DNA sequences that encode said polypeptides, without appreciable loss of their biological utility or activity. It is understood that codons capable of coding for such amino acid changes are known in the art.

In making such changes, the hydropathic index of amino acids may be considered. The importance of the hydropathic amino acid index in conferring interactive biological function on a protein is generally understood in the art (Kyte and Doolittle, *J. Mol. Biol.* 157, 105-132 (1982)). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, *J. Mol. Biol.* 157, 105-132 (1982)); these are isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (−4.5).

In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as govern by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0±1), glutamate (+3.0±1), scrine (+0.3), asparagine (+0.2), glutamine (+0.2), glycine (0), threonine (−0.4), proline (−0.5±1), alanine (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4).

In making such changes, the substitution of amino acids whose hydrophilicity values are within ±2 is preferred, those which are within ±1 are particularly preferred, and those within ±0.5 are even more particularly preferred.

In a further aspect of the present invention, one or more of the nucleic acid molecules of the present invention differ in nucleotide sequence from those encoding a *D. v. virgifera* protein or fragment thereof set forth in SEQ ID NO: 1 through SEQ ID NO: 9112 or fragment thereof due to the fact that one or more codons encoding an amino acid has been substituted for a codon that encodes a nonessential substitution of the amino acid originally encoded.

Isolation and identification of nucleic acids of the present invention are described in detail in Examples. All or a substantial portion of the nucleic acids of the present invention may be used to isolate cDNAs and nucleic acids encoding *D. v. virgifera* protein homologues or fragments thereof from the same or other species.

A "substantial portion" of a nucleotide sequence comprises enough of the sequence to afford specific identification and/or isolation of a nucleic acid fragment comprising the sequence. In general, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

Isolation of nucleic acids encoding protein homologues using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, structural nucleic acids encoding a *D. v. virgifera* protein or fragment thereof, either as cDNAs or genomic DNAs, could be isolated directly by using all or a portion of the nucleic acids of the present invention as DNA hybridization probes to screen cDNA or genomic libraries from any desired species employing methodology well known to those skilled in the art. Methods for forming such libraries are well known in the art. Specific oligonucleotide probes based upon the nucleic acids of the present invention can be designed and synthesized by methods known in the art. Moreover, the entire sequences of the nucleic acids cam be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the sequences. The resulting amplification products can be labeled directly during amplification reactions or labeled after amplification reactions, and used as probes to isolate full length cDNA or genomic DNAs under conditions of appropriate stringency.

Alternatively, the nucleic acids of interest can be amplified from nucleic acid samples using amplification techniques. For instance, the disclosed nucleic acids may be used to define a pair of primers that can be used with the polymerase chain reaction (Mullis, et al., *Cold Spring Harbor Symp. Quant. Biol.* 51:263-273 (1986); Erlich et al., EP 50,424; EP 84,796, EP 258,017, EP 237,362; Mullis, EP 201,184; Mullis et al., U.S. Pat. No. 4,683,202; Erlich, U.S. Pat. No. 4,582,788; and Saiki, R. et al., U.S. Pat. No. 4,683,194) to amplify and obtain any desired nucleic acid or fragment directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

In addition, two short segments of the nucleic acids of the present invention may be used in polymerase chain reaction protocols to amplify longer nucleic acids encoding *D. v. virgifera* protein homologues from DNA or RNA. For example, the skilled artisan can follow the RACE protocol (Frohman et al., Proc. Natl. Acad. Sci. USA 85:8998 (1988)) to generate cDNAs by using PCR to amplify copies of the region between a single point in the transcript and the 3' or 5' end. Primers oriented in the 3' and 5' directions can be designed from the nucleic acids of the present invention. Using commercially available 3'RACE or 5'RACE systems (Gibco BRL, Life Technologies, Gaithersburg, Md. U.S.A.), specific 3' or 5' cDNA fragments can be isolated (Ohara et al., Proc. Natl. Acad. Sci. USA 86:5673 (1989); Loh et al., Science 243:217

(1989)). Products generated by the 3' and 5' RACE procedures can be combined to generate full-length cDNAs (Frohman and Martin, Techniques 1: 165 (1989)).

Nucleic acids of interest may also be synthesized, either completely or in part, especially where it is desirable to provide plant-preferred sequences, by well-known techniques as described in the technical literature. See, e.g., Carruthers et al., Cold Spring Harbor Symp. Quant. Biol. 47:411-418 (1982), and Adams et al., J. Am. Chem. Soc. 105:661 (1983). Thus, all or a portion of the nucleic acids of the present invention may be synthesized using codons preferred by a selected host. Species-preferred codons may be determined, for example, from the codons used most frequently in the proteins expressed in a particular host species. Other modifications of the nucleotide sequences may result in mutants having slightly altered activity.

Availability of the nucleotide sequences encoding *D. v. virgifera* proteins or fragments thereof facilitates immunological screening of cDNA expression libraries. Synthetic polypeptides representing portions of the amino acid sequences of *D. v. virgifera* proteins or fragments thereof may be synthesized. These polypeptides can be used to immunize animals to produce polyclonal or monoclonal antibodies with specificity for polypeptides or proteins comprising the amino acid sequences. These antibodies can be then be used to screen cDNA expression libraries to isolate full-length cDNA clones of interest (Lerner, Adv. Immunol. 36: 1 (1984); Sambrook et al., Molecular Cloning: A Laboratory Manual; Cold Spring Harbor Laboratory Press: Cold Spring Harbor, (1989)). It is understood that people skilled in the art are familiar with the standard resource materials which describe specific conditions and procedures for the construction, manipulation and isolation of antibodies (see, for example, Harlow and Lane, In *Antibodies: A Laboratory Manual*, Cold Spring Harbor Press, Cold Spring Harbor, N.Y. (1988)).

Another aspect of the present invention relates to a method for obtaining a nucleic acid comprising a nucleotide sequence encoding a *D. v. virgifera* protein homologue. In a preferred embodiment, the method of the present invention for obtaining a nucleic acid encoding all or a substantial portion of the amino acid sequence of a *D. v. virgifera* protein comprising: (a) probing a cDNA or genomic library with a hybridization probe comprising all or a portion of a nucleotide sequence selected from the group consisting of SEQ ID NO:1 through SEQ ID NO:9112; (b) identifying a DNA clone that hybridizes with the hybridization probe; (c) isolating the DNA clone identified in step (b); and (d) sequencing the cDNA or genomic fragment that comprises the clone isolated in step (c) wherein the sequenced nucleic acid molecule encodes all or a substantial portion of the amino acid sequence of the *D. v. virgifera* protein homologue.

In another preferred embodiment, the method of the present invention for obtaining a nucleic acid fragment encoding a substantial portion of the amino acid sequence of a *D. v. virgifera* protein homologue comprising: (a) synthesizing a first and a second oligonucleotide primers corresponding to a portion of one of the sequences set forth in SEQ ID NO:1 through SEQ ID NO: 9112; and (b) amplifying a cDNA insert present in a cloning vector using the first and second oligonucleotide primers of step (a) wherein the amplified nucleic acid molecule encodes all or a substantial portion of the amino acid sequence of the *D. v. virgifera* protein homologue.

(b) Protein and Peptide Molecules

A class of agents comprises one or more of the protein or peptide molecules encoded by SEQ ID NO: 1 through SEQ ID NO:9112 or one or more of the protein or fragment thereof or peptide molecules encoded by other nucleic acid agents of the present invention. Protein and peptide molecules can be identified using known protein or peptide molecules as a target sequence or target motif in the BLAST programs of the present invention. In a preferred embodiment the protein or fragment molecules of the present invention are derived from *D. v. virgifera*.

The term "polypeptide", "peptide", or "protein", as used herein, refers to a polymer composed of amino acids connected by peptide bonds. The term applies to any amino acid polymers in which one or more amino acid residue is an artificial chemical analogue of a corresponding naturally occurring amino acid, as well as to any naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. It is well known in the art that proteins or polypeptides may undergo modification, including but not limited to, disulfide bond formation, gamma-carboxylation of glutamic acid residues, glycosylation, lipid attachment, phosphorylation, oligomerization, hydroxylation and ADP-ribosylation. Exemplary modifications are described in most basic texts, such as, for example, *Proteins—Structure and Molecular Properties,* 2nd ed., T. E. Creighton, W. H. Freeman and Company, New York (1993). Many detailed reviews are available on this subject, such as, for example, those provided by Wold, F., Post-translational Protein Modifications. Perspectives and Prospects, pp. 1-12 in *Post-translational Covalent Modification of Proteins*, B. C. Johnson, Ed., Academic Press, New York (1983); Seifter et al., Meth. Enzymol. 182:626-M (1990) and Rattan et al., *Protein Synthesis: Post-translational Modifications and Aging, Ann.* N.Y. Acad. Sci. 663:48-62 (1992). Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the polypeptide, a methionine residue at the $NH_2$ terminus may be deleted. Accordingly, this invention contemplates the use of both the methionine-containing and the methionin-less amino terminal variants of the protein of the invention. Thus, as used herein, the term "protein" or "polypeptide" includes any protein or polypeptide that is modified by any biological or non-biological process. The terms "amino acid" and "amino acids" refer to all naturally occurring amino acids and, unless otherwise limited, known analogs of natural amino acids that can function in a similar manner as naturally occurring amino acids. This definition is meant to include norleucine, ornithine, homocysteine, and homoserine.

One or more of the protein or fragment of peptide molecules may be produced via chemical synthesis, or more preferably, by expressing in a suitable bacterial or eukaryotic host. Suitable methods for expression are described by Sambrook, et al., (In: *Molecular Cloning, A Laboratory Manual, 2nd Edition, Cold Spring Harbor Press*, Cold Spring Harbor, N.Y. (1989)), or similar texts.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein. Such molecules may be derivatized to contain carbohydrate or other moieties (such as keyhole limpet hemocyanin, etc.). Fusion proteins or peptide molecules of the present invention are preferably produced via recombinant means.

Another class of agents comprise protein or peptide molecules encoded by SEQ ID NO: 1 through SEQ ID NO:9112 or, fragments or fusions thereof in which non-essential, or not relevant, amino acid residues have been added, replaced, or deleted. Such a homologue can be obtained by any of a variety of methods. Most preferably, as indicated above, one or more of the disclosed sequences (e.g., SEQ ID NO: 1 through SEQ ID NO:9112 or complements thereof) will be used to define a pair of primers that may be used to isolate the homologue-encoding nucleic acid molecules from any desired species. Such molecules can be expressed to yield homologues by recombinant means.

(c) Antibodies

One aspect of the present invention concerns antibodies, single-chain antigen binding molecules, or other proteins that specifically bind to one or more of the protein or peptide molecules of the present invention and their homologues, fusions or fragments. Such antibodies may be used to quantitatively or qualitatively detect the protein or peptide molecules of the present invention. As used herein, an antibody or peptide is said to "specifically bind" to a protein or peptide molecule of the present invention if such binding is not competitively inhibited by the presence of non-related molecules. In a preferred embodiment the antibodies of the present invention bind to proteins of the present invention. In a more preferred embodiment the antibodies of the present invention bind to proteins derived from *Diabrotica virgifera virgifera*.

Nucleic acid molecules that encode all or part of the protein of the present invention can be expressed, via recombinant means, to yield protein or peptides that can in turn be used to elicit antibodies that are capable of binding the expressed protein or peptide. Such antibodies may be used in immunoassays for that protein. Such protein-encoding molecules, or their fragments may be a "fusion" molecule (i.e., a part of a larger nucleic acid molecule) such that, upon expression, a fusion protein is produced. It is understood that any of the nucleic acid molecules of the present invention may be expressed, via recombinant means, to yield proteins or peptides encoded by these nucleic acid molecules.

The antibodies that specifically bind proteins and protein fragments of the present invention may be polyclonal or monoclonal, and may comprise intact immunoglobulins, or antigen binding portions of immunoglobulins (such as (F(ab'), F(ab')$_2$) fragments, or single-chain immunoglobulins producible, for example, via recombinant means). It is understood that practitioners are familiar with the standard resource materials which describe specific conditions and procedures for the construction, manipulation and isolation of antibodies (see, for example, Harlow and Lane, In *Antibodies: A Laboratory Manual*, Cold Spring Harbor Press, Cold Spring Harbor, N.Y. (1988)).

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as a fluorescent group, a radioisotope or an enzyme).

The ability to produce antibodies that bind the protein or peptide molecules of the present invention permits the identification of mimetic compounds of those molecules. A "mimetic compound" is a compound that is not that compound, or a fragment of that compound, but which nonetheless exhibits an ability to specifically bind to antibodies directed against that compound.

It is understood that any of the agents of the present invention can be substantially purified and/or be biologically active and/or recombinant.

(d) Insect Constructs and Transformed Insect Cells

The present invention also relates to an insect recombinant expression vectors comprising exogenous genetic material. The present invention also relates to an insect cell comprising an insect recombinant vector. The present invention also relates to methods for obtaining a recombinant insect host cell, comprising introducing into an insect cell exogenous genetic material.

The insect recombinant vector may be any vector which can be conveniently subjected to recombinant DNA procedures and can bring about the expression of the nucleotide sequence. The choice of a vector will typically depend on the compatibility of the vector with the insect host cell into which the vector is to be introduced. The vector may be a linear or a closed circular plasmid. The vector system may be a single vector or plasmid or two or more vectors or plasmids which together contain the total DNA to be introduced into the genome of the insect host. In addition, the insect vector may be an expression vector. Nucleic acid molecules can be suitable inserted into a replication vector for expression in the insect cell under a suitable promoter for insect cells. Many vectors are available for this purpose, and selection of the appropriate vector will depend mainly on the size of the nucleic acid molecule to be inserted into the vector and the particular host cell to be transformed with the vector. Each vector contains various components depending on its function (amplification of DNA or expression of DNA) and the particular host cell with which it is compatible. The vector components for insect cell transformation generally include, but not limited to, one or more of the following: a signal sequence, and origin of replication, one or more marker genes, and an inducible promoter.

The insect vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the insect cell, is integrated into the genome and replicated together with the chromosome(s) into which it has been integrated. For integration, the vector may rely on the nucleotide sequence of the vector for stable integration of the vector into the genome by homologous or nonhomologous recombination. Alternatively, the vector may contain additional nucleotide sequences for directing integration by homologous recombination into the genome of the insect host. The additional nucleotide sequences enable the vector to be integrated into the host cell genome at a precise location(s) in the chromosome(s). To increase the likelihood of integration at a precise location, there should be preferably two nucleotide sequences which individually contain a sufficient number of nucleic acids, preferably 400 bp to 1500 bp, more preferably 800 bp to 1000 bp, which are highly homologous with the corresponding target sequence to enhance the probability of homologous recombination. These nucleotide sequences may be any sequence that is homologous with a target sequence in the genome of the insect host cell, and, furthermore, may be non-encoding or encoding sequences.

Baculovirus expression vectors (BEVs) have become important tools for the expression of foreign genes, both for basic research and for the production of proteins with direct clinical applications in human and veterinary medicine (Doerfler, *Curr. Top. Microbiol. Immunol.* 131: 51-68 (1968); Luckow and Summers, *Bio/Technology* 6: 47-55 (1988a); Miller, *Annual Review of Microbiol.* 42: 177-199 (1988); Summers, *Curr. Comm. Molecular Biology*, Cold Spring Harbor Press, Cold Spring Harbor, N.Y. (1988); all of which are herein incorporated by reference in their entirety). BEVs are recombinant insect viruses in which the coding sequence for a chosen foreign gene has been inserted behind a baculovirus promoter in place of the viral gene, e.g., polyhedrin (Smith and Summers, U.S. Pat. No. 4,745,051, herein incorporated by reference in its entirety).

The use of baculovirus vectors relies upon the host cells being derived from Lepidopteran insects such as *Spodoptera frugiperda* or *Trichoplusia ni*. The preferred *Spodoptera frugiperda* cell line is the cell line Sf9. The *Spodoptera frugiperda* Sf9 cell line was obtained from American Type Culture Collection (Manassas, Va.) and is assigned accession number ATCC CRL 1711 (Summers and Smith, *A Manual of Methods for Baculovirus Vectors and Insect Cell Culture Procedures*, Texas Ag. Exper. Station Bulletin No. 1555 (1988), herein incorporated by reference in its entirety). Other insect cell systems, such as the silkworm *B. mori* may also be used.

The proteins expressed by the BEVs are, therefore, synthesized, modified and transported in host cells derived from Lepidopteran insects. Most of the genes that have been inserted and produced in the baculovirus expression vector system have been derived from vertebrate species. Other baculovirus genes in addition to the polyhedrin promoter may be employed to advantage in a baculovirus expression system. These include immediate-early (alpha), delayed-early (beta), late (gamma), or very late (delta), according to the phase of the viral infection during which they are expressed. The expression of these genes occurs sequentially, probably as the result of a "cascade" mechanism of transcriptional regulation. (Guarino and Summers, *J. Virol.* 57:563-571 (1986); Guarino and Summers, *J. Virol.* 61:2091-2099 (1987); Guarino and Summers, *Virol.* 162:444-451 (1988); all of which are herein incorporated by reference in their entirety).

Insect recombinant vectors are useful as an intermediates for the infection or transformation of insect cell systems. For example, an insect recombinant vector containing a nucleic acid molecule encoding a baculovirus transcriptional promoter followed downstream by an insect signal DNA sequence is capable of directing the secretion of the desired biologically active protein from the insect cell. The vector may utilize a baculovirus transcriptional promoter region derived from any of the over 500 baculoviruses generally infecting insects, such as for example the Orders Lepidoptera, Diptera, Orthoptera, Coleoptera and Hymenoptera, including for example but not limited to the viral DNAs of *Autographa caltformica* MNPV, *Bombyx mori* NPV, *Trichoplusia ni* MNPV, *Rachiplusia ou* MNPV or *Galleria mellonella* MNPV, wherein said baculovirus transcriptional promoter is a baculovirus immediate-early gene IEI or IEN promoter; an immediate-early gene in combination with a baculovirus delayed-early gene promoter region selected from the group consisting of 39K and a HindIII-k fragment delayed-early gene; or a baculovirus late gene promoter. The immediate-early or delayed-early promoters can be enhanced with transcriptional enhancer elements. The insect signal DNA sequence may code for a signal peptide of a Lepidopteran adipokinetic hormone precurser or a signal peptide of the *Manduca sexta* adipokinetic hormone precurser (Summers, U.S. Pat. No. 5,155,037; herein incorporated by reference in its entirety). Other insect signal DNA sequences include a signal peptide of the *Orthoptera Schistocerca gregaria* locust adipokinetic hormone precurser and the *Drosophila melanogaster* cuticle genes CP1, CP2, CP3 or CP4 or for an insect signal peptide having substantially a similar chemical composition and function (Summers, U.S. Pat. No. 5,155,037).

Insect cells are distinctly different from animal cells. Insects have a unique life cycle and have distinct cellular properties such as the lack of intracellular plasminogen activators in insect cells which are present in vertebrate cells. Another difference is the high expression levels of protein products ranging from 1 to greater than 500 mg/liter and the ease at which cDNA can be cloned into cells (Frasier, *In Vitro Cell. Dev. Biol.* 25:225 (1989); Summers and Smith, In: *A Manual of Methods for Baculovirus Vectors and Insect Cell Culture Procedures*, Texas Ag. Exper. Station Bulletin No. 1555 (1988), both of which are incorporated by reference in their entirety).

Recombinant protein expression in insect cells is achieved by viral infection or stable transformation. For viral infection, the desired gene is cloned into baculovirus at the site of the wild-type polyhedrin gene (Webb and Summers, *Technique* 2:173 (1990); Bishop and Posse, *Adv. Gene Technol.* 1:55 (1990); both of which are incorporated by reference in their entirety). The polyhedrin gene is a component of a protein coat in occlusions which encapsulate virus particles. Deletion or insertion in the polyhedrin gene results the failure to form occlusion bodies. Occlusion negative viruses are morphologically different from occlusion positive viruses and enable one skilled in the art to identify and purify recombinant viruses.

The vectors of present invention preferably contain one or more selectable markers which permit easy selection of transformed cells. A selectable marker is a gene the product of which provides, for example biocide or viral resistance, resistance to heavy metals, prototrophy to auxotrophs, and the like. Selection may be accomplished by co-transformation, e.g., as described in WO 91/17243, a nucleotide sequence of the present invention may be operably linked to a suitable promoter sequence. The promoter sequence is a nucleotide sequence which is recognized by the insect host cell for expression of the nucleotide sequence. The promoter sequence contains transcription and translation control sequences which mediate the expression of the protein or fragment thereof. The promoter may be any nucleotide sequence which shows transcriptional activity in the insect host cell of choice and may be obtained from genes encoding polypeptides either homologous or heterologous to the host cell.

For example, a nucleic acid molecule encoding a *D. v. virgifera* protein homologue or fragment thereof may also be operably linked to a suitable leader sequence. A leader sequence is a nontranslated region of a mRNA which is important for translation by the insect host. The leader sequence is operably linked to the 5' terminus of the nucleotide sequence encoding the protein or fragment thereof. The leader sequence may be native to the nucleotide sequence encoding the protein or fragment thereof or may be obtained from foreign sources. Any leader sequence which is functional in the insect host cell of choice may be used in the present invention.

A polyadenylation sequence may also be operably linked to the 3' terminus of the nucleotide sequence of the present invention. The polyadenylation sequence is a sequence which when transcribed is recognized by the insect host to add polyadenosine residues to transcribed mRNA. The polyadenylation sequence may be native to the nucleotide sequence encoding the protein or fragment thereof or may be obtained from foreign sources. Any polyadenylation sequence which is functional in the fungal host of choice may be used in the present invention.

To avoid the necessity of disrupting the cell to obtain the protein or fragment thereof, and to minimize the amount of possible degradation of the expressed polypeptide within the cell, it is preferred that expression of the polypeptide gene gives rise to a product secreted outside the cell. To this end, the protein or fragment thereof of the present invention may be linked to a signal peptide linked to the amino terminus of the protein or fragment thereof. A signal peptide is an amino acid sequence which permits the secretion of the protein or fragment thereof from the insect host into the culture medium. The signal peptide may be native to the protein or fragment thereof of the invention or may be obtained from foreign sources. The 5' end of the coding sequence of the nucleotide sequence of the present invention may inherently contain a signal peptide coding region naturally linked in translation reading frame with the segment of the coding region which encodes the secreted protein or fragment thereof.

At present, a mode of achieving secretion of a foreign gene product in insect cells is by way of the foreign gene's native signal peptide. Because the foreign genes are usually from non-insect organisms, their signal sequences may be poorly recognized by insect cells, and hence, levels of expression may be suboptimal. However, the efficiency of expression of foreign gene products seems to depend primarily on the characteristics of the foreign protein. On average, nuclear localized or non-structural proteins are most highly expressed, secreted proteins are intermediate, and integral membrane proteins are the least expressed. One factor generally affecting the efficiency of the production of foreign gene products in a heterologous host system is the presence of native signal sequences (also termed presequences, targeting signals, or leader sequences) associated with the foreign gene. The signal sequence is generally coded by a DNA sequence immediately following (5' to 3') the translation start site of the desired foreign gene.

The expression dependence on the type of signal sequence associated with a gene product can be represented by the following example: If a foreign gene is inserted at a site downstream from the translational start site of the baculovirus polyhedrin gene so as to produce a fusion protein (containing the N-terminus of the polyhedrin structural gene), the fused gene is highly expressed. But less expression is achieved when a foreign gene is inserted in a baculovirus expression vector immediately following the transcriptional start site and totally replacing the polyhedrin structural gene.

Insertions into the region −50 to −1 significantly alter (reduce) steady state transcription which, in turn, reduces translation of the foreign gene product. Use of the pVL941 vector optimizes transcription of foreign genes to the level of the polyhedrin gene transcription. Even though the transcription of a foreign gene may be optimal, optimal translation may vary because of several factors involving processing: signal peptide recognition, mRNA and ribosome binding, glycosylation, disulfide bond formation, sugar processing, oligomerization, for example.

The properties of the insect signal peptide are expected to be more optimal for the efficiency of the translation process in insect cells than those from vertebrate proteins. This phenomenon can generally be explained by the fact that proteins secreted from cells are synthesized as precursor molecules containing hydrophobic N-terminal signal peptides. The signal peptides direct transport of the select protein to its target membrane and are then cleaved by a peptidase on the membrane, such as the endoplasmic reticulum, when the protein passes through it.

Another exemplary insect signal sequence is the sequence encoding for Drosophila cuticle proteins such as CP1, CP2, CP3 or CP4 (Summers, U.S. Pat. No. 5,278,050; herein incorporated by reference in its entirety). Most of the 9 kb region of the Drosophila genome contains genes for the cuticle proteins has been sequenced. Four of the five cuticle genes contain a signal peptide coding sequence interrupted by a short intervening sequence (about 60 base pairs) at a conserved site. Conserved sequences occur in the 5' mRNA untranslated region, in the adjacent 35 base pairs of upstream flanking sequence and at −200 base pairs from the mRNA start position in each of the cuticle genes.

Standard methods of insect cell culture, cotransfection and preparation of plasmids are set forth in Summers and Smith (Summers and Smith, *A Manual of Methods for Baculovirus Vectors and Insect Cell Culture Procedures*, Texas Agricultural Experiment Station Bulletin No. 1555, Texas A&M University (1987)). Procedures for the cultivation of viruses and cells are described in Volkman and Summers, *J. Virol* 19: 820-832 (1975); Volkman et al., *J. Virol* 19: 820-832 (1976); and O'Reilly et al., Eds., Baculovirus Expression Vectors: A laboratory Manual, W.H. Freeman & Co., New York, N.Y. (1994); all of which are herein incorporated by reference in their entirety.

(e) Plant Constructs and Plant Transformants

The present invention also relates to a plant recombinant vector or construct comprising a structural nucleotide sequence encoding a *D. v. virgifera* protein or fragment thereof. The present invention also relates to a transformed plant cell or plant comprising in its genome an exogenous nucleic acid molecule encoding one or more *D. v. virgifera* proteins or fragments thereof. The present invention also relates to methods for creating a transgenic plant in which one or more *D. v. virgifera* proteins or fragments thereof are overexpressed.

By "exogenous" it is meant that a nucleic acid originates from outside the plant. An exogenous nucleic acid molecule can have a naturally occurring or non-naturally occurring nucleotide sequence. One skilled in the art understands that an exogenous nucleic acid molecule can be a heterologous nucleic acid derived from a different plant species than the plant into which the nucleic acid is introduced or can be a nucleic acid derived from the same plant species as the plant into which it is introduced.

The term "overexpression" refers to the expression of a polypeptide or protein encoded by an exogenous nucleic acid introduced into a host cell, wherein said polypeptide or protein is either not normally present in the host cell, or wherein said polypeptide or protein thereof is present in said host cell at a higher level than that normally expressed from the endogenous gene encoding said polypeptide or protein. By "endogenous gene" refers to a native gene in its natural location in the genome of an organism.

The term "genome" as it applies to plant cells encompasses not only chromosomal DNA found within the nucleus, but organelle DNA found within subcellular components of the cell. DNAs of the present invention introduced into plant cells can therefore be either chromosomally integrated or organelle-localized. The term "genome" as it applies to bacteria encompasses both the chromosome and plasmids within a bacterial host cell. Encoding DNAs of the present invention introduced into bacterial host cells can therefore be either chromosomally integrated or plasmid-localized.

Method which are well known to those skilled in the art may be used to construct the plant recombinant construct or vector of the present invention. These method include in vitro recombinant DNA techniques, synthetic techniques, and in vivo genetic recombination. Such techniques are described in Sambrook et al., Molecular Cloning, A Laboratory Manual, Cold Spring Harbor Press, Plainview, N.Y. (1989); and Ausubel et al., Current Protocols in Molecular Biology, John Wiley & Sons, New York, N.Y. (1989).

A plant recombinant construct or vector of the present invention contains a structural nucleotide sequence encoding one or more *D. v. virgifera* proteins or fragments thereof and operably linked regulatory sequences or control elements.

The term "operably linked", as used in reference to a regulatory sequence and a structural nucleotide sequence, means that the regulatory sequence causes regulated expression of the operably linked structural nucleotide sequence. "Expression" refers to the transcription and stable accumulation of sense or antisense RNA derived from the nucleic acid of the present invention. Expression may also refer to translation of mRNA into a polypeptide or protein. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-translated sequence, introns, or the coding sequence. "RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA.

"Regulatory sequences" or "control elements" refer to nucleotide sequences located upstream (5' noncoding sequences), within, or downstream (3' non-translated sequences) of a structural nucleotide sequence, and which influence the transcription, RNA processing or stability, or translation of the associated structural nucleotide sequence. Regulatory sequences may include promoters, translation leader sequences, introns, and polyadenylation recognition sequences.

The promoter sequence may consist of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions.

Promoters which are known or are found to cause transcription of DNA in plant cells can be used in the present invention. Such promoters may be obtained from a variety of sources such as plants and plant viruses. A number of promoters, including constitutive promoters, inducible promoters and tissue-specific promoters, that are active in plant cells have been described in the literature. It is preferred that the particular promoter selected should be capable of causing sufficient expression to result in the production of an effective amount of a protein to cause the desired phenotype. In addition to promoters that are known to cause transcription of DNA in plant cells, other promoters may be identified for use in the current invention by screening a plant cDNA library for genes that are selectively or preferably expressed in the target tissues and then determine the promoter regions.

The term "constitutive promoter" means a regulatory sequence which causes expression of a structural nucleotide sequence in most cells or tissues at most times. Constitutive promoters are active under most environmental conditions and states of development or cell differentiation. A variety of constitutive promoters are well known in the art. Examples of constitutive promoters that are active in plant cells include but are not limited to the nopaline synthase (NOS) promoters; the cauliflower mosaic virus (CaMV) 19S and 35S; the tobacco mosaic virus promoter; the figwort mosaic virus promoters; and actin promoters, such as the *Arabidopsis* actin gene promoter (see, e.g., Huang, Plant Mol. Biol. 33:125-139 (1997)).

The term "inducible promoter" refers to a regulatory sequence which causes conditional expression of a structural nucleotide sequence under the influence of changing environmental conditions or developmental conditions. Examples of inducible promoters include but are not limited to the light-inducible promoter from the small subunit of ribulose-1,5-bis-phosphate carboxylase (ssRUBISCO); the drought-inducible promoter of maize (Busk, Plant J. 11:1285-1295 (1997)); the cold, drought, and high salt inducible promoter from potato (Kirch, Plant Mol. Biol. 33:897-909 (1997)); a nitrate-inducible promoter derived from the spinach nitrite reductase gene (Back et al., Plant Mol. Biol. 17:9 (1991)); salicylic acid inducible promoter (Uknes et al., Plant Cell 5:159-169 (1993); Bi et al., Plant J. 8:235-245 (1995)); the auxin-response elements E1 promoter fragment (AuxREs) in the soybean (Glycine max L.) (Liu, Plant Physiol. 115:397-407 (1997)); the auxin-responsive *Arabidopsis* GST6 promoter (also responsive to salicylic acid and hydrogen peroxide) (Chen, Plant J. 10: 955-966 (1996)); the auxin-inducible parC promoter from tobacco (Sakai, 37:906-913 (1996)); a plant biotin response element (Streit, Mol. Plant. Microbe Interact. 10:933-937 (1997)); the promoter responsive to the stress honnone abscisic acid (Sheen, Science 274:1900-1902 (1996)); the maize In2-2 promoter activated by benzenesulfonamide herbicide safeners (De Vey Ider, Plant Cell Physiol. 38:568-577 (1997)); a tetracycline-inducible promoter, such as the promoter for the *Avena sativa* L. (oat) arginine decarboxylase gene (Masgrau, Plant J. 11:465-473 (1997)); and a salicylic acid-responsive element (Stange, Plant J. 11:1315-1324 (1997)).

The term "tissue-specific promoter" means a regulatory sequence that causes transcriptions or enhanced transcriptions of DNA in specific cells or tissues at specific times during plant development, such as in vegetative tissues or reproductive tissues. Examples of tissue-specific promoters under developmental control include promoters that initiate transcription only (or primarily only) in certain tissues, such as vegetative tissues, e.g., roots, leaves or stems, or reproductive tissues, such as fruit, ovules, seeds, pollen, pistils, flowers, or any embryonic tissue. Reproductive tissue specific promoters may be, e.g., ovule-specific, embryo-specific, endosperm-specific, integument-specific, seed coat-specific, pollen-specific, petal-specific, sepal-specific, or some combination thereof. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

A variety of promoters specifically active in vegetative tissues, such as leaves, stems, roots and tubers, can also be used to express the nucleic acids of the invention. Examples of tuber-specific promoters include but are not limited to the class I and II patatin promoters (Bevan et al., *EMBO J.* 8: 1899-1906 (1986); Koster-Topfer et al., *Mol Gen Genet.* 219: 390-396 (1989); Mignery et al., *Gene.* 62: 27-44 (1988); Jefferson et al., *Plant Mol. Biol.* 14: 995-1006 (1990)), the promoter for the potato tuber ADPGPP genes, both the large and small subunits; the sucrose synthase promoter (Salanoubat and Belliard, *Gene.* 60: 47-56 (1987), Salanoubat and Belliard, *Gene.* 84: 181-185 (1989)); and the promoter for the major tuber proteins including the 22 kd protein complexes and proteinase inhibitors (Hannapel, *Plant Physiol.* 101: 703-704 (1993)). Examples of leaf-specific promoters include but are not limited to the ribulose biphosphate carboxylase (RBCS or RuBISCO) promoters (see, e.g., Matsuoka, Plant J. 6:311-319 (1994)); the light harvesting chlorophyll a/b binding protein gene promoter (see, e.g., Shiina, Plant Physiol. 115-477-483 (1997); Casal, Plant Physiol. 116:1533-1538 (1998)); and the *Arabidopsis thaliana* myb-related gene promoter (Atmyb5) (Li, FEBS Lett. 379:117-121 (1996)). Examples of root-specific promoter include but are not limited to the promoter for the acid chitinase gene (Samac et al., *Plant Mol. Biol.* 25: 587-596 (1994)); the root specific subdomains of the CaMV35S promoter that have been identified (Lam et al., *Proc. Natl. Acad. Sci.* (*U.S.A.*) 86:7890-7894 (1989)); the ORF13 promoter from *Agrobacterium rhizogenes* which exhibits high activity in roots (Hansen, Mol. Gen. Genet. 254:337-343 (1997)); the promoter for the tobacco root-specific gene TobRB7 (Yamamoto, Plant Cell 3:371-382 (1991)); and the root cell specific promoters reported by Conkling et al. (Conkling et al., *Plant Physiol.* 93:1203-1211 (1990)).

Another class of useful vegetative tissue-specific promoters are meristermatic (root tip and shoot apex) promoters. For example, the "SHOOTMERISTEMLESS" and "SCARECROW" promoters, which are active in the developing shoot or root apical meristems (Di Laurenzio, Cell 86:423-433 (1996); Long, Nature 379:66-69 (1996)), can be used. Another example of a useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto, Plant Cell. 7:517-527 (1995)). Also another example of a useful promoter is that which controls the expression of knl-related genes from maize and other species which show meristern-specific expression (see, e.g., Granger, Plant Mol. Biol. 31:373-378 (1996); Kerstetter, Plant Cell 6:1877-1887 (1994); Hake, Philos. Trans. R. Soc. Lond. B. Biol. Sci. 350:45-51 (1995). Another example of a meristematic promoter is the *Arabidopsis thaliana* KNAT1 promoter. In the shoot apex, KNAT1 transcript is localized primarily to the shoot apical meristem; the expression of KNATI in the shoot meristem decreases during the floral transition and is restricted to the cortex of the inflorescence stem (see, e.g., Lincoln, Plant Cell 6:1859-1876 (1994)).

Suitable seed-specific promoters can be derived from the following genes: MAC1 from maize (Sheridan, Genetics 142: 1009-1020 (1996); Cat3 from maize (GenBank No. L05934, Abler, Plant Mol. Biol. 22:10131-1038 (1993); vivparous-1 from *Arabidopsis* (Genbank No. U93215); Atimyc1 from *Arabidopsis* (Urao, Plant Mol. Biol. 32:571-57 (1996); Conceicao, Plant 5:493-505 (1994); napA from *Brassica napus* (GenBank No. J02798); the napin gene family from *Brassica napus* (Sjodahl, Planta 197:264-271 (1995)).

The ovule-specific BEL1 gene described in Reiser (1995) Cell 83:735-742, GenBank No. U39944, can also be used. See also Ray (1994) Proc. Natl. Acad. Sci. USA 91:5761-5765. The egg and central cell specific FIEEI promoter is also a useful reproductive tissue-specific promoter.

A maize pollen-specific promoter has been identified in maize (Guerrero (1990) Mol. Gen. Genet. 224:161-168). Other genes specifically expressed in pollen are described, e.g., by Wakeley (1998) Plant Mol. Biol. 37:187-192; Ficker (1998) Mol. Gen. Genet. 257:132-142; Kulikauskas (1997) Plant Mol. Biol. 34:809-814; Treacy (1997) Plant Mol. Biol. 34:603-611.

Promoters derived from genes encoding embryonic storage proteins, which includes the gene encoding the 2S storage protein from *Brassica napus* (Dasgupta, Gene 133:301-302 (1993); the 2s seed storage protein gene family from *Arabidopsis*; the gene encoding oleosin 20 kD from *Brassica napus* (GenBank No. M63985); the genes encoding oleosin A (Genbank No. U09118) and oleosin B (Genbank No. U09119) from soybean; the gene encoding oleosin from *Arabidopsis* (Genbank No. Z17657); the gene encoding oleosin 18 kD from maize (GenBank No. J05212, Lee, Plant Mol. Biol. 26:1981-1987 (1994)); and the gene encoding low molecular weight sulphur rich protein from soybean (Choi, Mol Gen, Genet. 246:266-268 (1995)), can also be used.

Promoters derived from genes encoding for zein genes (including the 15 kD, 16 kD, 19 kD, 22 kD, 27 kD, and gamma genes) (Pedersen et al., *Cell* 29: 1015-1026 (1982)) can be also used. The zeins are a group of storage proteins found in maize endosperm.

Other promoters known to function, for example, in maize, include the promoters for the following genes: waxy, Brittle, Shrunken 2, Branching enzymes I and II, starch synthases, debranching enzymes, oleosins, glutelins, and sucrose synthases. A particularly preferred promoter for maize endosperm expression is the promoter for the glutelin gene from rice, more particularly the Osgt-1 promoter (Zheng et al., *Mol. Cell. Biol.* 13: 5829-5842 (1993), herein incorporated by reference in its entirety). Examples of promoters suitable for expression in wheat include those promoters for the ADPglucose pyrophosphorylase (ADPGPP) subunits, the granule bound and other starch synthases, the branching and debranching enzymes, the embryogenesis-abundant proteins, the gliadins, and the glutenins. Examples of such promoters in rice include those promoters for the ADPGPP subunits, the granule hound and other starch synthases, the branching enzymes, the debranching enzymes, sucrose synthases, and the glutelins. A particularly preferred promoter is the promoter for rice glutelin, Osgt-1. Examples of such promoters for barley include those for the ADPGPP subunits, the granule bound and other starch synthases, the branching enzymes, the debranching enzymes, sucrose synthases, the hordeins, the embryo globulins, and the aleurone specific proteins.

A tomato promoter active during fruit ripening, senescence and abscission of leaves and, to a lesser extent, of flowers can be used (Blume, Plant J. 12:731-746 (1997)). Other exemplary promoters include the pistol specific promoter in the potato (*Solarium tuberosum* L.) SK2 gene, encoding a pistil-specific basic endochitinase (Ficker, Plant Mol. Biol. 35:425-431 (1997)); the Blec4 gene from pea (*Pisum sativum* cv. Alaska), active in epidermal tissue of vegetative and floral shoot apices of transgenic alfalfa. This makes it a useful tool to target the expression of foreign genes to the epidermal layer of actively growing shoots. The tissue specific E8 promoter from tomato is also useful for directing gene expression in fruits.

It is recognized that additional promoters that may be utilized are described, for example, in U.S. Pat. Nos. 5,378,619, 5,391,725, 5,428,147, 5,447,858, 5,608,144, 5,608,144, 5,614,399, 5,633,441, 5,633,435, and 4,633,436, all of which are herein incorporated in their entirety. In addition, a tissue specific enhancer may be used (Fromm et al., *The Plant Cell* 1:977-984 (1989), herein incorporated by reference in its entirety). It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) Molecular Biotechnology 3:225).

The "3' non-translated sequences" refer to DNA sequences located downstream of a structural nucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA-precursor. The polyadenylation sequence can be derived from the natural gene, from a variety of plant genes, or from T-DNA. An example of the polyadenylation sequence is the nopaline synthase 3' sequence (NOS 3'; Fraley et al., Proc. Natl. Acad. Sci. USA 80: 4803-4807 (1983)). The use of different 3' non-translated sequences is exemplified by Ingelbrecht et al., Plant Cell 1:671-680 (1989).

Generally, optimal expression in monocotyledonous and some dicotyledonous plants is obtained when an intron sequence is inserted between the promoter sequence and the structural gene sequence or, optionally, may be inserted in the structural coding sequence to provide an interrupted coding sequence. An example of such an intron sequence is the HSP 70 intron described in WO 93/19189.

A recombinant vector or construct of the present invention will typically comprise a selectable marker which confers a selectable phenotype on plant cells. Selectable markers may also be used to select for plants or plant cells that contain the exogenous nucleic acids encoding polypeptides or proteins of the present invention. The marker may encode biocide resistance, antibiotic resistance (e.g., kanamycin, G418 bleomycin, hygromycin, etc.), or herbicide resistance (e.g., glyphosate, etc.). Examples of selectable markers include, but are not limited to, a neo gene (Potrykus et al., *Mol. Gen. Genet.* 199:183-188 (1985)) which codes for kanamycin resistance and can be selected for using kanamycin, G418, etc.; a bar gene which codes for bialaphos resistance; a mutant EPSP synthase gene (Hinchee et al., *Bio/Technology* 6:915-922 (1988)) which encodes glyphosate resistance; a nitrilase gene which confers resistance to bromoxynil (Stalker et al., *J. Biol. Chem.* 263:6310-6314 (1988)); a mutant acetolactate synthase gene (ALS) which confers imidazolinone or sulphonylurea resistance (European Patent Application 154,204 (Sep. 11, 1985)); and a methotrexate resistant DHFR gene (Thillet et al., *J. Biol. Chem.* 263:12500-12508 (1988)).

A recombinant vector or construct of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson, *Plant Mol. Biol, Rep.* 5:387-405 (1987); Jefferson et al., *EMBO J.* 6:3901-3907 (1987)); an R-locus gene, which encodes a product that regulates the production of anthocyanin pigments (red color) in plant tissues (Dellaporta et al., Stadler Symposium 11:263-282 (1988)); a β-lactamase gene (Sutcliffe et al., *Proc. Natl. Acad. Sci.* (*U.S.A.*) 75:3737-3741 (1978)), a gene which encodes an enzyme for which various chromogenic substrates are known (e.g., PADAC, a chromogenic cephalosporin); a luciferase gene (Ow et al., *Science* 234:856-859 (1986)) a xylE gene (Zukowsky et al., *Proc. Natl. Acad. Sci.* (*U.S.A.*) 80:1101-1105 (1983)) which encodes a catechol dioxygenase that can convert chromogenic catechols; an α-amylase gene (Ikatu et al., *Bio/Technol.* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins detectable, e.g., by ELISA, small active enzymes detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

In addition to a selectable marker, it may be desirous to use a reporter gene. In some instances a reporter gene may be used with or without a selectable marker. Reporter genes are genes which are typically not present in the recipient organism or tissue and typically encode for proteins resulting in some phenotypic change or enzymatic property. Examples of such genes are provided in K. Wising et al. Ann. Rev. Genetics, 22, 421 (1988), which is incorporated herein by reference. Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al., (1987 Biochem. Soc. Trans. 15, 17-19) to identify transformed cells.

In preparing the DNA constructs of the present invention, the various components of the construct or fragments thereof will normally be inserted into a convenient cloning vector, e.g., a plasmid that is capable of replication in a bacterial host, e.g., *E. coli*. Numerous vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

A recombinant vector or construct of the present invention may also include a chloroplast transit peptide, in order to target the polypeptide or protein of the present invention to the plastid. The term "plastid" refers to the class of plant cell organelles that includes amyloplasts, chloroplasts, chromoplasts, elaioplasts, eoplasts, etioplasts, leucoplasts, and proplastids. These organelles are self-replicating, and contain what is commonly referred to as the "chloroplast genome," a circular DNA molecule that ranges in size from about 120 to about 217 kb, depending upon the plant species, and which usually contains an inverted repeat region. Many plastid-localized proteins are expressed from nuclear genes as precursors and are targeted to the plastid by a chloroplast transit peptide (CTP), which is removed during the import steps. Examples of such chloroplast proteins include the small subunit of ribulose-1,5-biphosphate carboxylase (ssRUBISCO, SSU), 5-enolpyruvateshikimate-3-phosphate synthase (EPSPS), ferredoxin, ferredoxin oxidoreductase, the light-harvesting-complex protein I and protein II, and thioredoxin F. It has been demonstrated that non-plastid proteins may be targeted to the chloroplast by use of protein fusions with a CTP and that a CTP sequence is sufficient to target a protein to the plastid. Those skilled in the art will also recognize that various other chimeric constructs can be made that utilize the functionality of a particular plastid transit peptide to import the enzyme into the plant cell plastid depending on the promoter tissue specificity.

The present invention also provide a transgenic plant comprising in its genome an isolated nucleic acid which comprises: (A) a 5' non-coding sequence which functions in the cell to cause the production of a mRNA molecule; which is linked to (B) a structural nucleotide sequence, wherein the structural nucleotide sequence encodes a *D. v. virgifera* proteins or fragments thereof; which is linked to (C) a 3' non-translated sequence that functions in said cell to cause termination of transcription.

The term "transgenic plant" refers to a plant that contains an exogenous nucleic acid, which can be derived from the same plant species or from a different plant species. Transgenic plants are also meant to comprise progeny (decendant, offspring, etc.) of any generation of such a transgenic plant. A seed of any generation of all such transgenic plants wherein said seed comprises a DNA sequence encoding the protein or fragment thereof of the present invention is also an important aspect of the invention.

The DNA constructs of the present invention may be introduced into the genome of a desired plant host by a variety of conventional transformation techniques, which are well known to those skilled in the art. Preferred methods of transformation of plant cells or tissues are the *Agrobacterium* mediated transformation method and the biolistics or particle-gun mediated transformation method. Suitable plant transformation vectors for the purpose of *Agrobacterium* mediated transformation include those derived from a Ti plasmid of *Agrobacterium tumefaciens*, as well as those disclosed, e.g., by Herrera-Estrella et al., Nature 303:209 (1983); Bevan, Nucleic Acids Res. 12: 8711-8721 (1984); Klee et al., Bio-Technology 3(7): 637-642 (1985); and EPO publication 120,516. In addition to plant transformation vectors derived from the Ti or root-inducing (Ri) plasmids of *Agrobacterium*, alternative methods can be used to insert the DNA constructs of this invention into plant cells. Such methods may involve, but are not limited to, for example, the use of liposomes, electroporation, chemicals that increase free DNA uptake, free DNA delivery via microprojectile bombardment, and transformation using viruses or pollen.

A plasmid expression vector suitable for the introduction of a nucleic acid encoding a polypeptide or protein of the present invention in monocots using electroporation or particle-gun mediated transformation is composed of the following: a promoter that is constitutive or tissue-specific; an intron that provides a splice site to facilitate expression of the gene, such as the Hsp70 intron (PCT Publication WO93/19189); and a 3' polyadenylation sequence such as the nopaline synthase 3' sequence (NOS 3'; Fraley et al., Proc. Natl. Acad. Sci. USA 80: 4803-4807 (1983)). This expression cassette may be assembled on high copy replicons suitable for the production of large quantities of DNA.

An example of a useful Ti plasmid cassette vector for plant transformation is pMON17227. This vector is described in PCT Publication WO 92/04449 and contains a gene encoding an enzyme conferring glyphosate resistance (denominated CP4), which is an excellent selection marker gene for many plants. The gene is fused to the *Arabidopsis* EPSPS chloroplast transit peptide (CTP2) and expressed from the FMV promoter as described therein.

When adequate numbers of cells (or protoplasts) containing the exogenous nucleic acid encoding a polypeptide or protein of the present invention are obtained, the cells (or protoplasts) are regenerated into whole plants. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, canola/rapeseed, etc.), Cucurbitaceae (melons and cucumber), Gramineae (wheat, barley, rice, maize, etc.), Solanaceae (potato, tobacco, tomato, peppers), various floral crops, such as sunflower, and nut-bearing trees, such as almonds, cashews, walnuts, and pecans. See, for example, Ammirato et al., Handbook of Plant Cell Culture—Crop Species. Macmillan Publ. Co. (1984); Shimamoto et al., Nature 338:274-276 (1989); Fromm, UCLA Symposium on Molecular Strategies for Crop Improvement, Apr. 16-22, 1990. Keystone, Colo. (1990); Vasil et al., Bio/Technology 8:429-434 (1990); Vasil et al., Bio/Technology 10:667-674 (1992); Hayashimoto, Plant Physiol. 93:857-863 (1990); and Datta et al., Bio-technology 8:736-740 (1990). Regeneration can also be obtained from plant callus, explants, organs, or parts thereof. Such regeneration techniques are described generally in Klee et al., Ann. Rev. Plant Phys. 38:467-486 (1987).

A transgenic plant formed using *Agrobacterium* transformation methods typically contains a single exogenous gene on one chromosome. Such transgenic plants can be referred to as being heterozygous for the added exogenous gene. More preferred is a transgenic plant that is homozygous for the added exogenous gene; i.e., a transgenic plant that contains two added exogenous genes, one gene at the same locus on each chromosome of a chromosome pair. A homozygous transgenic plant can be obtained by sexually mating (selfing) an independent segregant transgenic plant that contains a single exogenous gene, germinating some of the seed produced and analyzing the resulting plants produced for the exogenous gene of interest.

The development or regeneration of transgenic plants containing the exogenous nucleic acid that encodes a polypeptide or protein of interest is well known in the art. Preferably, the regenerated plants are self-pollinated to provide homozygous transgenic plants, as discussed above. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide or protein of the present invention is cultivated using methods well known to one skilled in the art.

Transgenic plants, that can be generated by practice of the present invention, include but are not limited to Acacia, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, cherry, cilantro, citrus, clementines, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, Loblolly pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, turf, a vine, watermelon, wheat, yams, and zucchini.

The present invention also provides parts of the transgenic plants of present invention. Plant parts, without limitation, include seed, endosperm, ovule and pollen. In a particularly preferred embodiment of the present invention, the plant part is a seed.

The present invention also further provides method for generating a transgenic plant comprising the steps of: a) introducing into the genome of the plant an exogenous nucleic acid, wherein the exogenous nucleic acid comprises in the 5' to 3' direction i) a promoter that functions in the cells of said plant, said promoter operably linked to; ii) a structural nucleic acid sequence encoding a *D. v. virgifera* protein or fragment thereof, said structural nucleic acid sequence operably linked to; iii) a 3' non-translated nucleic acid sequence that functions in said cells of said plant to cause transcriptional termination; b) obtaining transformed plant cells containing the nucleic acid sequence of step (a); and c) regenerating from said transformed plant cells a transformed plant in which said polypeptide or protein is overexpressed.

Any of the isolated nucleic acid molecules of the present invention may be introduced into a plant cell in a permanent or transient manner in combination with other genetic elements such as vectors, promoters, enhancers etc. Further any of the nucleic acid molecules encoding a *D. v. virgifera* protein or fragment thereof may be introduced into a plant cell in a manner that allows for over expression of the protein or polypeptide encoded by the nucleic acid molecule.

Antibodies have been expressed in plants (Hiatt et al., *Nature* 342:76-78 (1989); Conrad and Fielder, *Plant Mol. Biol.* 26:1023-1030 (1994)). Cytoplasmic expression of a scFv (single-chain Fv antibodies) has been reported to delay infection by artichoke mottled crinkle virus. Transgenic plants that express antibodies directed against endogenous proteins may exhibit a physiological effect (Philips et al., *EMBO J.* 16:4489-4496 (1997); Marion-Poll, *Trends in Plant Science* 2:447-448 (1997)). For example, expressed anti-abscisic antibodies reportedly result in a general perturbation of seed development (Philips et al., *EMBO J.* 16:4489-4496 (1997)).

Antibodies that are catalytic may also be expressed in plants (abzymes). The principle behind abzymes is that since antibodies may be raised against many molecules, this recognition ability can be directed toward generating antibodies that bind transition states to force a chemical reaction forward (Persidas, *Nature Biotechnology* 15:1313-1315 (1997); Baca et al., *Ann. Rev. Biophys. Biomol. Struct.* 26:461-493 (1997)). The catalytic abilities of abzymes may be enhanced by site directed mutagenesis. Examples of abzymes are, for example, set forth in U.S. Pat. No. 5,658,753; U.S. Pat. No. 5,632,990; U.S. Pat. No. 5,631,137; U.S. Pat. No. 5,602,015; U.S. Pat. No. 5,559,538; U.S. Pat. No. 5,576,174; U.S. Pat. No. 5,500,358; U.S. Pat. No. 5,318,897; U.S. Pat. No. 5,298,409; U.S. Pat. No. 5,258,289 and U.S. Pat. No. 5,194,585, all of which are herein incorporated in their entirety.

It is understood that any of the antibodies of the present invention may be expressed in plants and that such expression can result in a physiological effect. It is also understood that any of the expressed antibodies may be catalytic.

(f) Microbial Constructs and Transformed Microbial Cells

The nucleotide sequences of the present invention may be introduced into a wide variety of prokaryotic and eukaryotic microorganism hosts to express the *D. v. virgifera* proteins or fragments thereof of interest. The term "microorganism" includes prokaryotic and eukaryotic microbial species such as bacteria and fungi. Fungi include yeast and filamentous fungi. Illustrative prokaryotes, both Gram-negative and Gram-positive, include Enterobacteriaceae, such as *Escherichia, Erwinia, Shigella, Salmonella*, and *Proteus*; Bacillaceae; Rhizobiceae, such as *Rhizobium*; Spirillaceae, such as *photobacterium, Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae, Actinomycetales, and Nitrohacteraceae. Among eukaryotes are fungi, such as *Phycomycetes* and *Ascomycetes*, which includes yeast, such as *Saccharomyces* and *Schizosaccharomyces*; and *Basidiomycetes* yeast, such as *Rhodotorula, Aureobasidium, Sporobolomyces*, and the like.

For the purpose of plant protection against insects, a large number of microorganisms known to inhabit the phylloplane (the surface of the plant leaves) and/or the rhizosphere (the soil surrounding plant roots) of a wide variety of important crops may also be desirable host cells for manipulation, propagation, storage, delivery and/or mutagenesis of the disclosed recombinant constructs. These microorganisms include bacteria, algae, and fungi. Of particular interest are microorganisms, such as bacteria, e.g., genera *Bacillus* (including the species and subspecies *B. thuringiensis kurstaki* HD-1, *B. thuringiensis kurstaki* HD-73, *B. thuringiensis sotto, B. thuringiensis berliner, B. thuringiensis thuringiensis, B. thuringiensis tolworthi, B. thuringiensis dendrolimus, B. thuringiensis alesti, B. thuringiensis galleriae, B. thuringiensis aizawai, B. thuringiensis subtoxicus, B. thuringiensis entomocidus, B. thuringiensis tenebrionis* and *B. thuringiensis san diego*); *Pseudomonas, Erwinia, Serratia, Klebsiella, Zanthomonas, Streptomyces, Rhizobium, Rhodopseudomonas, Methylophilius, Agrobacterium, Acetobacter, Lactobacillus, Arthrobacter, Azotobacter, Leuconostoc*, and *Alcaligenes*; fungi, particularly yeast, e.g., genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Rhodobacter sphaeroides, Xanthomonas campestris, Rhizobium melioti, Alcaligenes eutrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*.

It is well known that exogenous nucleic acids encoding polypeptides of interest can be introduced into a microbial host cell, such as a bacterial cell or a fungal cell, using a recombinant construct. The present invention also relates to a fungal or bacterial recombinant construct comprising a structural nucleotide sequence encoding a *D. v. virgifera* protein or fragment thereof. The present invention also relates to a bacterial or fungal cell comprising a bacterial or fungal recombinant vector of the present invention. The present invention also relates to methods for obtaining a recombinant bacterial or fungal host cell, comprising introducing into a bacterial or fungal host cell an exogenous nucleic acid molecule of the present invention.

The bacterial recombinant vector may be a linear or a closed circular plasmid. The vector system may be a single vector or plasmid or two or more vectors or plasmids which together contain the total DNA to be introduced into the genome of the bacterial host. In addition, the bacterial vector may be an expression vector. Nucleic acid molecules encoding *D. v. virgifera* proteins or fragments thereof can, for example, be suitably inserted into a replicable vector for expression in a bacterium under the control of a suitable promoter for that bacterium. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more selectable marker genes, and an inducible promoter allowing the expression of exogenous DNA.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene* 2:95 (1977)). pBR322 contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

Nucleic acid molecules encoding *D. v. virgifera* proteins or fragments thereof may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide encoding DNA that is inserted into the vector. The heterologous signal sequence selected should be one that is recognized and processed (i.e., cleaved by a signal peptidase) by the host cell. For bacterial host cells that do not recognize and process the native polypeptide signal sequence, the signal sequence is substituted by a bacterial signal sequence selected, for example, from the group consisting of the alkaline phosphatase, β-lactamase, or heat-stable enterotoxin II leaders and the like.

Both expression and cloning vectors contain a nucleotide sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria.

Expression and cloning vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*. One example of a selection scheme utilizes a drug to arrest growth of a host cell. Those cells that are successfully transformed with a heterologous protein or fragment thereof produce a protein conferring drug resistance and thus survive the selection regimen.

The expression vector for producing a polypeptide can also contains an inducible promoter that is recognized by the host bacterial organism and is operably linked to the nucleic acid encoding, for example, the nucleic acid molecule encoding the *D. v. virgifera* protein or fragment thereof of interest. Inducible promoters suitable for use with bacterial hosts include the β-lactamase, *E. coli* λ phage $P_L$ and $P_R$, and *E. coli* galactose, arabinose, alkaline phosphatase, tryptophan (trp), and lactose operon promoter systems and variations thereof (Chang et al., *Nature* 275:615 (1978); Goeddel et al., *Nature* 281:544 (1979); Guzman et al., *J. Bacteriol.* 174:7716-7728 (1992); Goeddel, *Nucleic Acids Res.* 8:4057 (1980); EP 36,776) and hybrid promoters such as the tac promoter (deBoer et al., *Proc. Natl. Acad. Sci.* (*USA*) 80:21-25 (1983)). However, other known bacterial inducible promoters are suitable (Siebenlist et al., *Cell* 20:269 (1980)).

Promoters for use in bacterial systems also generally contain a Shine-Dalgarno (S.D.) sequence or a consensus sequence thereof operably linked to the DNA encoding the polypeptide of interest. The promoter can be removed from the bacterial source DNA by restriction enzyme digestion and inserted into the vector containing the desired DNA coding sequence, or vice versa.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (E.P.O. Pub. No. 127,328). Integrating vectors may also be comprised of bacteriophage or transposon sequences.

Construction of suitable vectors containing one or more of the above-listed components employs standard recombinant DNA techniques. Isolated plasmids or DNA fragments are cleaved, tailored, and re-ligated in the form desired to generate the plasmids required. Examples of available bacterial expression vectors include, but are not limited to, the multifunctional *E. coli* cloning and expression vectors such as Bluescript™ (Stratagene, La Jolla, Calif.), in which, for example, a *D. v. virgifera* protein or fragment thereof, may be ligated into the vector in frame with sequences for the amino-terminal Met and the subsequent 7 residues of β-galactosidase so that a hybrid protein is produced; pIN vectors (Van Heeke and Schuster *J. Biol. Chem.* 264:5503-5509 (1989)); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

It is, of course, necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYC177, or pKN410 are used to supply the replicon. *E. coli* strain W3110 is a preferred host or parent host because it is a common host strain for recombinant DNA product fermentations. Preferably, the host cell should secrete minimal amounts of proteolytic enzymes.

Host cells are transfected and preferably transformed with the above-described vectors and cultured in conventional nutrient media modified as appropriate for inducing promoters, selecting transformants, or amplifying the genes encoding the desired sequences.

Numerous methods of transfection are known to the ordinarily skilled artisan, for example, calcium phosphate and electroporation. Depending on the host cell used, transformation is done using standard techniques appropriate to such cells. The calcium treatment employing calcium chloride, as described in section 1.82 of Sambrook et al., *Molecular Cloning: A Laboratory Manual*, New York: Cold Spring Harbor Laboratory Press, (1989), is generally used for bacterial cells that contain substantial cell-wall barriers. Another method for transformation employs polyethylene glycol/DMSO, as described in Chung and Miller (Chung and Miller, *Nucleic Acids Res.* 16:3580 (1988)). Yet another method is the use of the technique termed electroporation. In addition, bacterial cells can be readily transformed using various forms of phages (i.e., transducing, temperate, lytic and lysogenic), suicide vectors for inserting DNA directly into the chromosome, and through homologous recombination using either phages, suicide vectors or linear DNA.

Bacterial cells used to produce the polypeptide of interest for purposes of this invention are cultured in suitable media in which the promoters for the nucleic acid encoding the heterologous polypeptide can be artificially induced as described generally, e.g., in Sambrook et al., *Molecular Cloning: A Laboratory Manual*, New York: Cold Spring Harbor Laboratory Press, (1989). Examples of suitable media are given in U.S. Pat. Nos. 5,304,472 and 5,342,763.

A yeast recombinant construct can typically include one or more of the following: a promoter sequence, fusion partner sequence, leader sequence, transcription termination sequence, a selectable marker. These elements can be combined into an expression cassette, which may be maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24 (Botstein et al., Gene, 8:17-24 (1979)), pC1/1 (Brake et al., Proc. Natl. Acad. Sci. USA, 81:4642-4646 (1984)), and YRp17 (Stinchcomb et al., J. Mol. Biol., 158:157 (1982)). In addition, a replicon may be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20.

Useful yeast promoter sequences can be derived from genes encoding enzymes in the metabolic pathway. Examples of such genes include alcohol dehydrogenase (ADH) (E.P.O. Pub. No. 284044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (E.P.O. Pub. No. 329203). The yeast PHO5 gene, encoding acid phosphatase, also provides useful promoter sequences (Myanohara et al., Proc. Natl. Acad. Sci. USA, 80:1 (1983)). In addition, synthetic promoters which do not occur in nature also function as yeast promoters. Examples of such hybrid promoters include the ADH regulatory sequence linked to the GAP transcription activation region (U.S. Pat. Nos. 4,876, 197 and 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (E.P.O. Pub. No. 164556). Furthermore, a yeast promoter can include naturally occurring promoters of non-yeast origin that have the ability to bind yeast RNA polymerase and initiate transcription. Examples of such promoters include, inter alia, (Cohen et al., Proc. Natl. Acad. Sci. USA, 77:1078 (1980); Henikoff et al., Nature 283:835 (1981); Hollenberg et al., Curr. Topics Microbiol. Immunol., 96:119 (1981); Mercerau-Puigalon et al., Gene, 11:163 (1980); and Panthier et al., Curr. Genet., 2:109 (1980)).

Intracellularly expressed fusion proteins provide an alternative to direct expression of the polypeptides of interest. Typically, a DNA sequence encoding the N-terminal portion of a stable protein, a fusion partner, is fused to the 5' end of heterologous structural nucleotide sequence encoding the desired polypeptide. Upon expression, this construct will provide a fusion of the two amino acid sequences. The DNA sequence at the junction of the two amino acid sequences may or may not encode a cleavable site. See, e.g., E.P.O. Pub. No. 196056. Another example is a ubiquitin fusion protein. Such a ubiquitin fusion protein preferably retains a site for a processing enzyme (e.g. ubiquitin-specific processing protease) to cleave the ubiquitin from the polypeptide of the present invention. Through this method, therefore, a mature polypeptide can be isolated [see, P.C.T. WO 88/024066].

Alternatively, polypeptides or proteins can also be secreted from the cell into the growth media by creating chimeric DNA molecules that encode a fusion protein comprised of a leader sequence fragment that provides for secretion in yeast of the polypeptides. Preferably, there are processing sites encoded between the leader fragment and the polypeptide-encoding sequence fragment that can be cleaved either in vivo or in vitro. The leader sequence fragment typically encodes a signal peptide comprised of hydrophobic amino acids which direct the secretion of the protein from the cell.

DNA encoding suitable signal sequences can be derived from genes for secreted yeast proteins, such as the yeast invertase gene (E.P.O. Pub. No. 12873; J.P.O. Pub. No. 62,096,086) and the A-factor gene (U.S. Pat. No. 4,588,684). Alternatively, leaders of non-yeast origin, such as an interferon leader, exist that also provide for secretion in yeast (E.P.O. Pub. No. 60057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (typically about 25 to about 50 amino acid residues) (U.S. Pat. Nos. 4,546,083 and 4,870,008; and E.P.O. Pub. No. 324274). Additional leaders employing an alpha-factor leader fragment that provides for secretion include hybrid alpha-factor leaders made with a pre-sequence of a first yeast, but a pro-region from a second yeast alpha factor. See, e.g., P.C.T. WO 89/02463.

Examples of transcription terminator sequence and other yeast-recognized termination sequences, such as those coding for glycolytic enzymes, are known to those of skill in the art.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. Integrations appear to result from recombinations between homologous DNA in the vector and the yeast chromosome (Orr-Weaver et al., Methods in Enzymol., 101:228-245 (1983)). An integrating vector may be directed to a specific locus in yeast by selecting the appropriate homologous sequence for inclusion in the vector. See Orr-Weaver et al., supra. One or more expression constructs may integrate, possibly affecting levels of recombinant protein produced (Rine et al., Proc. Natl. Acad. Sci. USA, 80:6750 (1983)). The chromosomal sequences included in the vector can occur either as a single segment in the vector, which results in the integration of the entire vector, or as two segments homologous to adjacent segments in the chromosome and flanking the expression construct in the vector, which results in the stable integration of only the expression construct.

Expression and transformation vectors, either extrachromosomal replicons or integrating vectors, have been developed for transformation into many yeasts. For example, expression vectors have been developed for, inter alia, the following yeasts: *Candida albicans* (Kurtz, et al., Mol. Cell. Biol., 6:142 (1986)), *Candida maltosa* (Kunze et al., J. Basic Microbiol., 25:141 (1985)); *Hansenula polymorpha* (Gleeson et al., J. Gen. Microbiol. 132:3459 (1986); Roggenkamp et al., Mol. Gen. Genet. 202:302 (1986)); *Kluyveromyces fragilis* (Das et al., J. Bacteriol. 158:1165 (1984)); *Kluyveromyces lactic* (De Louvencourt et al., J. Bacteriol. 154:737 (1983); Van den Berg et al., Bio/Technology 8:135 (1990)); *Pichia guillerimondii* (Kunze et al., J. Basic Microbiol. 25:141 (1985)); *Pichia pastoris* (Cregg et al., Mol. Cell. Biol. 5:3376 (1985); U.S. Pat. Nos. 4,837,148 and 4,929,555); *Saccharomyces cerevisiae* (Hinnen et al., Proc. Natl. Acad. Sci. USA 75:1929 (1978); Ito et al., J. Bacteriol. 153:163 (1983)); *Schizosaccharomyces pombe* (Beach and Nurse, Nature 300:706 (1981)); and *Yarrowia lipolytica* (Davidow, et al., Curr. Genet. 10:380471 (1985); and Gaillardin et al., Curr. Genet. 10:49 (1985)).

Methods of introducing exogenous nucleic acids into yeast hosts are well-known in the art, and typically include either the transformation of spheroplasts or of intact yeast cells treated with alkali cations. Transformation procedures usually vary with the yeast species to be transformed. See e.g., Kurtz et al., Mol. Cell. Biol. 6:142 (1986); Kunze et al., J. Basic Microbiol. 25:141 (1985) for *Candida*. See, e.g., Gleeson et al., J. Gen. Microbiol. 132:3459 (1986); Roggenkamp et al., Mol. Gen. Genet. 202:302 (1986) for *Hansenula*. See, e.g., Das et al., J. Bacteriol. 158:1165 (1984); De Louvencourt et al., J. Bacteriol. 154:1165 (1983); Van den Berg et al., Bio/Technology 8:135 (1990) for *Kluyveromyces*. See, e.g., Cregg et al., Mol. Cell. Biol. 5:3376 (1985); Kunze et al., J. Basic Microbiol. 25:141 (1985); U.S. Pat. Nos. 4,837,148 and 4,929,555 for *Pichia*. See, e.g., Hinnen et al., Proc. Natl. Acad. Sci. USA 75:1929 (1978); Ito et al., J. Bacteriol. 153: 163 (1983) for *Saccharomyces*. See, e.g., Beach and Nurse, Nature 300:706 (1981) for *Schizosaccharomyces*. See, e.g., Davidow et al., Curr. Genet. 10:39 (1985); Gaillardin et al., Curr. Genet. 10:49 (1985) for *Yarrowia*.

In order to obtain expression polypeptides or proteins of interest, recombinant microbial host cells derived from the transformants are incubated under conditions which allow expression of the recombinant polypeptide-encoding sequence. These conditions will vary, dependent upon the host cell selected. However, the conditions are readily ascertainable to those of ordinary skill and knowledge in the art.

Detection of polypeptides expressed in the transformed host cell may be performed by several methods. For example, a polypeptide or protein may be detected by its immunological reactivity with antibodies.

Polypeptides or proteins of the present invention may be isolated from the cell by lysis, if formed intracellularly, or isolated from the culture medium, if secreted, by conventional methods.

(g) Mammalian Constructs and Transformed Mammalian Cells

The present invention also relates to a mammalian recombinant expression vector comprising exogenous genetic material. The present invention also relates to a mammalian cell comprising a mammalian recombinant expression vector. The present invention also relates to methods for obtaining a recombinant mammalian host cell, comprising introducing into a mammalian cell exogenous genetic material.

The mammalian recombinant expression vector may be any vector which can be conveniently subjected to recombinant DNA procedures. Many vectors are available for this purpose, and a suitable expression vector is one that is compatible with the desired function (e.g., transient expression, long term expression, integration, replication, amplification) and in which the control elements are compatible with the host cell. The control elements are those non-translated regions of the vector—promoters, enhancers, 5' and 3' untranslated regions—which interact with host celluar proteins to carry out transcription and translation.

Vectors suitable for replication in mammalian cells may include viral replicons, or sequences that ensure integration of the sequence encoding *D. v. virgifera* protein homologues or fragments thereof into the host genome. Suitable vectors may include, for example, those derived from simian virus SV40, retroviruses, bovine papilloma virus, vaccinia virus, and adenovirus. The components of the vectors, e.g. replicons, selection genes, enhancers, promoters, and the like, may be obtained from natural sources or synthesized by known procedures. (See, Kaufman et al, J. Mol. Biol., 159:511-521 (1982); and Kaufman, Proc. Natl. Acad. Sci., USA, 82:689-693 (1985)).

A suitable vector may be one derived from vaccinia viruses. In this case, a nucleic acid molecule encoding a *D. v. virgifera* protein homologue or fragment thereof is inserted into the vaccinia genome. Techniques for the insertion of foreign DNA into the vaccinia virus genome are known in the art, and utilize, for example, homologous recombination. The insertion of the foreign DNA is generally into a gene which is non-essential in nature, for example, the thymidine kinase gene (tk), which also provides a selectable marker. Plasmid shuttle vectors that greatly facilitate the construction of recombinant viruses have been described (see, for example, Mackett et al, *J. Virol.* 49: 857 (1984); Chakrabarti et al., *Mol. Cell. Biol.* 5: 3403 (1985); Moss, In: *Gene Transfer Vectors*

*For Mammalian Cells* (Miller and Calos, eds., Cold Spring Harbor Laboratory, N.Y., p. 10, (1987)). Expression of the *D. v. virgifera* protein homologues or fragments thereof then occurs in cells or animals which are infected with the live recombinant vaccinia virus.

Suitable mammalian expression vectors usually contain one or more eukaryotic control elements that are capable of expression in mammalian cells. The control element is comprised of at least a promoter to mediate transcription of foreign DNA sequences. Suitable promoters for mammalian cells are known in the art and include viral promoters such as that from simian virus 40 (SV40), cytomegalovirus (CMV), Rous sarcoma virus (RSV), adenovirus (ADV), and bovine papilloma virus (BPV).

In addition, the control element may also be comprised of a termination sequence and poly(A) addition sequences which are operably linked to nucleotide sequences encoding *D. v. virgifera* protein homologues or fragments thereof. The control element may also be comprised of an enhancer sequence which increases the expression of *D. v. virgifera* protein homologues or fragments thereof.

Furthermore, the control element may also be comprised of an enhancer, which is any regulatory DNA sequence that can stimulate transcription up to 1000-fold when linked to endogenous or heterologous promoters, with synthesis beginning at the normal mRNA start site. Enhancers are also active when they are placed upstream or downstream from the transcription initiation site, in either normal or flipped orientation, or at a distance of more than 1000 nucleotides from the promoter (Maniatis et al. Science, 236:1237 (1987); Alberts et al., Molecular Biology of the Cell, 2nd ed. (1989)). Enhancers derived from viruses may be particularly useful, because they typically have a broader host range. Examples include the SV40 early gene enhancer (Dijkema et al, EMBO J., 4:761 (1985)) and the enhancer/promoters derived from the long terminal repeat (LTR) of the Rous Sarcoma Virus (Gorman et al., Proc. Natl. Acad. Sci. 79:6777 (1982b)) and from human cytomegalovirus (Boshart et al., Cell, 41:521 (1985)). Additionally, some enhancers are regulatable and become active only in the presence of an inducer, such as a hormone or metal ion (Sansone-Corsi and Borelli, Trends Genet. 2:215 (1986); Maniatis et al. Science, 236:1237 (1987)).

Where selection is intended, sequences which encode selectable markers may also be included in the vector. Selectable markers for mammalian cells are known in the art, and include for example, thymidine kinase, dihydrofolate reductase (together with methotrexate as a DHFR amplifier), aminoglycoside phosphotransferase, hygromycin B phosphotransferase, asparagine synthetase, adenosine deaminase, metallothionien, and antibiotic resistant genes such as neomycin.

For homologous recombination, constructs can be prepared where the amplifiable gene will be flanked, normally on both sides with DNA homologous with the DNA of the target region. Depending upon the nature of the integrating DNA and the purpose of the integration, the homologous DNA will generally be within 100 kb, usually 50 kb, preferably about 25 kb, of the transcribed region of the target gene, more preferably within 2 kb of the target gene. Where modeling of the gene is intended, homology will usually be present proximal to the site of the mutation. By gene is intended the coding region and those sequences required for transcription of a mature mRNA. The homologous DNA may include the 5'-upstream region outside of the transcriptional regulatory region or comprising any enhancer sequences, transcriptional initiation sequences, adjacent sequences, or the like. The homologous region may include a portion of the coding region, where the coding region may be comprised only of an open reading frame or combination of exons and introns. The homologous region may comprise all or a portion of an intron, where all or a portion of one or more exons may also be present. Alternatively, the homologous region may comprise the 3'-region, so as to comprise all or a portion of the transcriptional termination region, or the region 3' of this region. The homologous regions may extend over all or a portion of the target gene or be outside the target gene comprising all or a portion of the transcriptional regulatory regions and/or the structural gene.

The integrating constructs may be prepared in accordance with conventional ways, where sequences may be synthesized, isolated from natural sources, manipulated, cloned, ligated, subjected to in vitro mutagenesis, primer repair, or the like. At various stages, the joined sequences may be cloned, and analyzed by restriction analysis, sequencing, or the like. Usually during the preparation of a construct where various fragments are joined, the fragments, intermediate constructs and constructs will be carried on a cloning vector comprising a replication system functional in a prokaryotic host, e.g., *E. coli*, and a marker for selection, e.g., biocide resistance, complementation to an auxotrophic host, etc. Other functional sequences may also be present, such as polylinkers, for ease of introduction and excision of the construct or portions thereof, or the like. A large number of cloning vectors are available such as pBR322, the pUC series, etc. These constructs may then be used for integration into the primary mammalian host.

The mammalian cell expression vectors described herein may be synthesized by techniques well known to those skilled in this art. Other appropriate expression vectors of which numerous types are known in the art for mammalian expression can also be used for this purpose.

Mammalian cell lines available as hosts for expression are known in the art and include many immortalized cell lines available from the American Type Culture Collection (ATCC). Exemplary mammalian host cells include particularly primate cell lines and rodent cell lines, including transformed cell lines. Suitable cell lines include, but are not limited to, Chinese hamster ovary (CHO) cells, HeLa cells, baby hamster kidney (BHK) cells, monkey kidney cells (COS-1), human hepatocellular carcinoma cells (e.g., Hep G2), human adenovirus transformed 293 cells, mouse L-929 cells, HaK hamster cell lines, murine 3T3 cells derived from Swiss, Balb-c or NIH mice and a number of other cell lines.

The DNA can be introduced into the expression host by a variety of techniques that include calcium phosphate/DNA co-precipitates, microinjection of DNA into the nucleus, electroporation, yeast protoplast fusion with intact cells, transfection, polycations, e.g., polybrene, polyornithine, etc., or the like. The DNA may be single or double stranded DNA, linear or circular. The various techniques for transforming mammalian cells are well known (see Keown et al., *Methods Enzymol*. (1989), Keown et al., *Methods Enzymol*. 185:527-537 (1990); Mansour et al., *Nature* 336:348-352, (1988)).

(h) Computer Media

The nucleotide sequence provided in SEQ ID NO:1, through SEQ ID NO:9112 or fragment thereof, or complement thereof, or a nucleotide sequence at least 90% identical, preferably 95%, identical even more preferably 99% or 100% identical to the sequence provided in SEQ ID NO:1 through SEQ ID NO:9112 or fragment thereof, or complement thereof, can be "provided" in a variety of mediums to facilitate use. Such a medium can also provide a subset thereof in a form that allows a skilled artisan to examine the sequences.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc, storage medium, and magnetic tape: optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention.

As used herein, "recorded" refers to a process for storing information on computer readable medium. A skilled artisan can readily adopt any of the presently known methods for recording information on computer readable medium to generate media comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the nucleotide sequence information of the present invention.

By providing one or more of nucleotide sequences of the present invention, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., *J. Mol. Biol.* 215: 403-410 (1990)) and BLAZE (Brutlag, et al., *Comp. Chem.* 17: 203-207 (1993)) search algorithms on a Sybase system can be used to identify open reading frames (ORFs) within the genome that contain homology to ORFs or proteins from other organisms. Such ORFs are protein-encoding fragments within the sequences of the present invention and are useful in producing commercially important proteins such as enzymes used in amino acid biosynthesis, metabolism, transcription, translation, RNA processing, nucleic acid and a protein degradation, protein modification, and DNA replication, restriction, modification, recombination, and repair.

The present invention further provides systems, particularly computer-based systems, which contain the sequence information described herein. Such systems are designed to identify commercially important fragments of the nucleic acid molecule of the present invention. As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based system are suitable for use in the present invention.

As indicated above, the computer-based systems of the present invention comprise a data storage means having stored therein a nucleotide sequence of the present invention and the necessary hardware means and software means for supporting and implementing a search means. As used herein, "data storage means" refers to memory that can store nucleotide sequence information of the present invention, or a memory access means which can access manufactures having recorded thereon the nucleotide sequence information of the present invention. As used herein, "search means" refers to one or more programs which are implemented on the computer-based system to compare a target sequence or target structural motif with the sequence information stored within the data storage means. Search means are used to identify fragments or regions of the sequence of the present invention that match a particular target sequence or target motif. A variety of known algorithms are disclosed publicly and a variety of commercially available software for conducting search means are available can be used in the computer-based systems of the present invention. Examples of such software include, but are not limited to, MacPattern (EMBL), BLASTIN and BLASTIX (NCBIA). One of the available algorithms or implementing software packages for conducting homology searches can be adapted for use in the present computer-based systems.

The most preferred sequence length of a target sequence is from about 10 to 100 amino acids or from about 30 to 300 nucleotide residues. However, it is well recognized that during searches for commercially important fragments of the nucleic acid molecules of the present invention, such as sequence fragments involved in gene expression and protein processing, may be of shorter length.

As used herein, "a target structural motif," or "target motif," refers to any rationally selected sequence or combination of sequences in which the sequences the sequence(s) are chosen based on a three-dimensional configuration which is formed upon the folding of the target motif. There are a variety of target motifs known in the art. Protein target motifs include, but are not limited to, enzymatic active sites and signal sequences. Nucleic acid target motifs include, but are not limited to, promoter sequences, cis elements, hairpin structures and inducible expression elements (protein binding sequences).

Thus, the present invention further provides an input means for receiving a target sequence, a data storage means for storing the target sequences of the present invention sequence identified using a search means as described above, and an output means for outputting the identified homologous sequences. A variety of structural formats for the input and output means can be used to input and output information in the computer-based systems of the present invention. A preferred format for an output means ranks fragments of the sequence of the present invention by varying degrees of homology to the target sequence or target motif. Such presentation provides a skilled artisan with a ranking of sequences which contain various amounts of the target sequence or target motif and identifies the degree of homology contained in the identified fragment.

A variety of comparing means can be used to compare a target sequence or target motif with the data storage means to identify sequence fragments sequence of the present invention. For example, implementing software which implement the BLAST and BLAZE algorithms (Altschul et al., *J. Mol. Biol.* 215: 403-410 (1990)) can be used to identify open frames within the nucleic acid molecules of the present invention. A skilled artisan can readily recognize that any one of the publicly available homology search programs can be used as the search means for the computer-based systems of the present invention.

Uses of the Agents of the Present Invention

Nucleic acid molecules and fragments thereof of the present invention may be employed to obtain other nucleic acid molecules from other species. Such nucleic acid molecules include the nucleic acid molecules that encode the complete coding sequence of a protein and promoters and flanking sequences of such molecules. In addition, such nucleic acid molecules include nucleic acid molecules that encode for other isozymes or gene family members. Such molecules can be readily obtained by using the above-described nucleic acid molecules or fragments thereof to screen cDNA or genomic libraries obtained from *D. v. virgifera*. Methods for forming such libraries are well known in the art.

Nucleic acid molecules and fragments thereof of the present invention may also be employed to obtain other nucleic acid molecules such as nucleic acid homologues. Such homologues include the nucleic acid molecules that encode, in whole or in part, protein homologues of other species, plants or other organisms. Such molecules can be readily obtained by using the above-described nucleic acid molecules or fragments thereof to screen cDNA or genomic libraries. Methods for forming such libraries are well known in the art. Such homologue molecules may differ in their nucleotide sequences from those found in one or more of SEQ ID NO:1 through SEQ ID NO:9112 or complements thereof because complete complementarity is not needed for stable hybridization. The nucleic acid molecules of the present invention therefore also include molecules that, although capable of specifically hybridizing with the nucleic acid molecules may lack "complete complementarity." In a particular embodiment, methods or 3' or 5' RACE may be used to obtain such sequences (Frohman, M. A. et al., *Proc. Natl. Acad. Sci. (U.S.A.)* 85:8998-9002 (1988); Ohara, O. et al., *Proc. Natl. Acad. Sci. (U.S.A.)* 86:5673-5677 (1989)).

Any of a variety of methods may be used to obtain one or more of the above-described nucleic acid molecules (Zamechik et al., *Proc. Natl. Acad. Sci. (U.S.A.)* 83: 4143-4146 (1986); Goodchild et al., *Proc. Natl. Acad. Sci. (U.S.A.)* 85: 5507-5511 (1988); Wickstrom et al., *Proc. Natl. Acad. Sci. (U.S.A.)* 85: 1028-1032 (1988); Holt et al., *Molec. Cell. Biol.* 8: 963-973 (1988); Gerwirtz et al., *Science* 242: 1303-1306 (1988); Anfossi et al., *Proc. Natl. Acad. Sci. (U.S.A.)* 86: 3379-3383 (1989); Becker et al., *EMBO J.* 8: 3685-3691 (1989)). Automated nucleic acid synthesizers may be employed for this purpose. In lieu of such synthesis, the disclosed nucleic acid molecules may be used to define a pair of primers that can be used with the polymerase chain reaction (Mullis et al., *Cold Spring Harbor Symp. Quant. Biol.* 51: 263-273 (1986); Erlich et al., European Patent 50,424; European Patent 84,796, European Patent 258,017, European Patent 237,362; Mullis, European Patent 201,184; Mullis et al., U.S. Pat. No. 4,683,202; Erlich, U.S. Pat. No. 4,582,788; and Saiki, R. et al., U.S. Pat. No. 4,683,194) to amplify and obtain any desired nucleic acid molecule or fragment.

Nucleic acid molecules and fragments thereof of the present invention may also be employed to create/identify affinity reagents which are capable of a) seeking and binding to expressed proteins and b) verifying that the protein is expressed on insect gut surface as evidenced by binding (for example, by using immunofluorescence). Examples of affinity reagents include but are not limited to RNA aptamers, high-affinity antibodies and peptide aptamers.

RNA aptamers are oligonucleotide ligands, usually single-stranded RNA, which have high affinity for specific proteins. RNA aptamers can be selected in vitro by the SELEX (Systemic Evolution of Ligands by Exponential Enrichment) methodology. Such methodology comprises: transcribing a DNA library; selecting RNA for binding; and reverse transcribing and amplifying over several rounds the bound RNA to produce a product capable of binding the desired target (Tuerk and Gold, *Science* 249:505-510 (1990); Gold et al., *Annu. Rev. Biochem.* 64, 763-797 (1995)).

Other examples of methods to generate affinity reagents include phage display technology, ribosome display technology and conventional technology for monoclonal antibodies.

Phage display technology refers to a selection process of phage library, which expresses a highly diverse combinatorial immunoglobulin library. The selection process involves the sequential enrichment of specific binding phage from a large excess of nonbinding clones, which is achieved by multiple rounds of phage binding to the target, washing to remove nonspecific binding phage, elution to retrieve specific binding phage and amplification of specific phage after infection of *Escherichia coli*. Any method that separates clones that bind from those that do not can be used as a selection method. Examples of selection methods includes but are not limited to biopanning on immobilized antigen on plastic plates, columns or BIAcore, or selection using biotinylated antigen. The selection and phage-retrieval methods are known to those of skill in the art and are described in the literature (for example, see Winter et al., *Annu. Rev. Immunol.* 12: 433-455 (1994); McCafferty, Hoogenboom, & Chiswell, *Antibody Engineering, a Practical Approach*. IRL Press, Oxford, UK (1996); Hoogenboom, *Trends Biotechnol.* 15: 62-70 (1997); and Griffiths et al, EMBO; 13:3245-3260 (1994)).

Ribosome display technology refers to a methodology of phenotypic selection for ligand binding with a complete, native protein molecule in vitro (Hanes and Pluckthun, *Proc. Natl. Acad. Sci. USA* 94: 4937-4942 (1997)). Such method comprises: (1) first amplifying by PCR a DNA library, whereby introducing a T7 promoter, ribosome-binding site, and stem-loops, and then transcribing DNA to RNA; (2) translating mRNA after purification in vitro in an expression system; (3) after translation affinity-selecting desired ribosome complexes from the translation mixture by binding to the immobilized antigen and removing unspecific ribosome complexes by intensive washing; (4) dissociating the bound ribosome complexes or specifically eluting whole complexes with antigen; (5) isolating RNA from the complexes; (6) reverse transcribing isolated mRNA to cDNA and then PCR amplifying the cDNA; and (7) using the PCR amplified DNA in step 6 for the next cycle of enrichment.

Peptide aptamers are proteins that contain a conformationally constrained peptide region of variable sequence displayed from a scaffold. Peptide aptamers can be generated using phage display technology or ribosome display technology or conventional technology for monoclonal antibodies.

Peptide aptamers from combinatorial libraries can be dominant inhibitors of gene function. For example, peptide aptamers can be used to inhibit the pathway of interest in the cells expressing the peptide aptamers and to identify mutants with phenotypes of interest. C R Geyer, A Colman-Lerner, R Brent; PNAS 96 (1999)8567-8572.

A biologically active compound can be conjugated to an affinity reagent to produce a chimeric protein that both binds the target and produces a desirable biological functionality. For example, a binding reagent could be fused to the functional domain of the Bt protein (domain 2) to produce a novel protein capable of binding proteins other than its target protein (e.g., aminopeptidase), producing septicemia similar to that seen with Bt toxicity. In addition, the aptamer itself may have biological activity in addition to the affinity to the expressed cDNA protein.

Promoter sequence(s) and other genetic elements including but not limited to transcriptional regulatory elements associated with one or more of the disclosed nucleotide sequences can also be obtained using the disclosed nucleotide sequences provided herein. In one embodiment, such sequences are obtained by incubating EST nucleic acid molecules or preferably fragments thereof with members of genomic libraries and recovering clones that hybridize to the EST nucleic acid molecule or fragment thereof. In a second embodiment, methods of "chromosome walking," or inverse PCR may be used to obtain such sequences (Frohman, et al., *In Proc. Natl. Acad. Sci.* (*U.S.A.*) 85:8998-9002 (1988); Ohara, et al., *Proc. Natl. Acad. Sci.* (*U.S.A.*) 86: 5673-5677 (1989); Pang et al., *Biotechniques,* 22(6); 1046-1048 (1977); Huang et al., *Methods Mol. Biol.* 69: 89-96 (1977); Hard et al., *Methods Mol. Biol.* 58: 293-301 (1996)). In one embodiment, the disclosed ESTs are used to identify cDNAs whose analogous genes contain promoters with desirable expression patterns. Isolation and functional analysis of the 5' flanking promoter sequences of these genes from genomic libraries, for example, using genomic screening methods and PCR techniques would result in the isolation of useful promoters and transcriptional regulatory elements. These methods are known to those of skill in the art and have been described (See for example Birren et al., *Genome Analysis:Analyzing DNA,* 1, (1997), Cold Spring Harbor Laboratory Press, Cold Spring Harbor, N.Y.). Promoters obtained utilizing the ESTs of the present invention could also be modified to affect their control characteristics. Examples of such modifications would include but are not limited to enhancer sequences as reported by Kay et al., *Science* 236:1299 (1987).

In one aspect of the present invention, an evaluation can be conducted to determine whether a particular mRNA molecule is present. One or more of the nucleic acid molecules of the present invention, preferably one or more of the EST nucleic acid molecules of the present invention are utilized to detect the presence or quantity of the mRNA species. Such molecules are then incubated with cell or tissue extracts of a plant under conditions sufficient to permit nucleic acid hybridization. The detection of double-stranded probe-mRNA hybrid molecules is indicative of the presence of the mRNA; the amount of such hybrid formed is proportional to the amount of mRNA. Thus, such probes may be used to ascertain the level and extent of the mRNA production in a plant's cells or tissues. Such nucleic acid hybridization may be conducted under quantitative conditions (thereby providing a numerical value of the amount of the mRNA present). Alternatively, the assay may be conducted as a qualitative assay that indicates either that the mRNA is present, or that its level exceeds a user set, predefined value.

A principle of in situ hybridization is that a labeled, single-stranded nucleic acid probe will hybridize to a complementary strand of cellular DNA or RNA and, under the appropriate conditions, these molecules will form a stable hybrid. When nucleic acid hybridization is combined with histological techniques, specific DNA or RNA sequences can be identified within a single cell. An advantage of in situ hybridization over more conventional techniques for the detection of nucleic acids is that it allows an investigator to determine the precise spatial population (Angerer et al., *Dev. Biol.* 101: 477-484 (1984); Angerer et al., *Dev. Biol.* 112: 157-166 (1985); Dixon et al., *EMBO J.* 10: 1317-1324 (1991)). In situ hybridization may be used to measure the steady-state level of RNA accumulation. It is a sensitive technique and RNA sequences present in as few as 5-10 copies per cell can be detected (Hardin et al., *J. Mol. Biol.* 202: 417-431 (1989)). A number of protocols have been devised for in situ hybridization, each with tissue preparation, hybridization, and washing conditions (Meyerowitz, *Plant Mol. Biol. Rep.* 5: 242-250 (1987); Cox and Goldberg, In: *Plant Molecular Biology: A Practical Approach* (ed. C. H. Shaw), pp. 1-35. IRL Press, Oxford (1988); Raikhel et al., *In situ RNA hybridization in plant tissues*. In *Plant Molecular Biology Manual*, vol. B9: 1-32. Kluwer Academic Publisher, Dordrecht, Belgium (1989)).

In situ hybridization also allows for the localization of proteins within a tissue or cell (Wilkinson, *In Situ Hybridization*, Oxford University Press, Oxford (1992); Langdale, *In Situ Hybridization* 165-179 In: *The Maize Handbook*, eds. Freeling and Walbot, Springer-Verlag, New York (1994)). It is understood that one or more of the molecules of the present invention, preferably one or more of the EST nucleic acid molecules of the present invention or one or more of the antibodies of the present invention may be utilized to detect the expression level or pattern of a protein or mRNA thereof by in situ hybridization.

Fluorescent in situ hybridization also enables the localization of a particular DNA sequence along a chromosome which is useful, among other uses, for gene mapping, following chromosomes in hybrid lines or detecting chromosomes with translocations, transversions or deletions. In situ hybridization has been used to identify chromosomes in several plant species (Griffor et al., *Plant Mol. Biol.* 17: 101-109 (1991); Gustafson et al., *Proc. Nat'l. Acad. Sci.* (*U.S.A.*). 87: 1899-1902 (1990); Mukai and Gill, *Genome* 34: 448-452. (1991); Schwarzacher and Heslop-Harrison, *Genome* 34: 317-323 (1991); Wang et al., *Jpn. J. Genet.* 66: 313-316 (1991); Parra and Windle, *Nature Genetics,* 5: 17-21 (1993)). It is understood that the nucleic acid molecules of the present invention may be used as probes or markers to localize sequences along a chromosome.

It is also understood that one or more of the molecules of the present invention, preferably one or more of the EST nucleic acid molecules of the present invention or one or more of the antibodies of the present invention may be utilized to detect the expression level or pattern of a protein or mRNA thereof by in situ hybridization.

Further, it is also understood that any of the nucleic acid molecules of the present invention may be used as marker nucleic acids and or probes in connection with methods that require probes or marker nucleic acids. As used herein, a probe is an agent that is utilized to determine an attribute or feature (e.g. presence or absence, location, correlation, identity, etc.) or a molecule, cell, tissue or plant. As used herein, a marker nucleic acid is a nucleic acid molecule that is utilized to determine an attribute or feature (e.g., presence or absence, location, correlation, etc.) or a molecule, cell, tissue or plant.

Nucleic acid molecules of the present invention can be used to monitor expression. A microarray-based method for high-throughput monitoring of gene expression may be utilized to measure gene-specific hybridization targets. This 'chip'-based approach involves using microarrays of nucleic acid molecules as gene-specific hybridization targets to quantitatively measure expression of the corresponding genes (Schena et al., *Science* 270: 467-470 (1995); Shalon, Ph.D. Thesis, Stanford University (1996)). Every nucleotide in a large sequence can be queried at the same time. Hybridization can be used to efficiently analyze nucleotide sequences.

Several methods have been described for fabricating microarrays of nucleic acid molecules and using such microarrays in detecting nucleotide sequences. For instance, microarrays can be fabricated by spotting nucleic acid molecules, e.g. genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Useful substrates for arrays include nylon, glass and silicon. See, for instance, U.S. Pat. Nos. 5,202,231; 5,445,934; 5,525,464; 5,700,637; 5,744,305; 5,800,992. Sequences can be efficiently analyzed by hybridization to a large set of oligonucleotides or cDNA molecules representing a large portion of genes of a genome. An array consisting of oligonucleotides or cDNA molecules complementary to subsequences of a target sequence can be used to determine the identity of a target sequence, measure its amount, and detect differences between the target and a reference sequence. Nucleic acid molecule microarrays may also be screened with molecules or fragments thereof to determine nucleic acid molecules that specifically bind molecules or fragments thereof.

A nucleic acid "library" encompassed by the present invention also includes biochemical libraries of the nucleic acids of SEQ ID NOS:1-9112, e.g., collections of nucleic acids representing the provided nucleic acids. The biochemical libraries can take a variety of forms, e.g. a solution of cDNAs, a pattern of probe nucleic acids stably bound to a surface of a solid support (microarray) and the like. By array is meant an article of manufacture that has a solid support or substrate with one or more nucleic acid targets on one of its surfaces, where the number of distinct nucleic acid sequences may be in the tens, or even hundreds, or even thousand, or even tens of thousands. Each nucleic acid will comprise at 18 consecutive covalently linked nucleotides, and often at least 25 consecutive covalently linked nucleotides, and often at least 100 to 1000 consecutive covalently linked nucleotides, and may represent up to a complete coding sequence or cDNA. A variety of different array formats have been developed and are known to those of skill in the art. The arrays of the subject invention find use in a variety of applications, including gene expression analysis, drug screening, mutation analysis and the like, as disclosed in the above-listed exemplary patent documents.

In addition to the above nucleic acid libraries, analogous libraries of polypeptides are also provided, where the where the polypeptides of the library will represent at least a portion of the polypeptides encoded by SEQ ID NOS:1-9112.

The microarray approach may also be used with polypeptide targets (U.S. Pat. No. 5,445,934; U.S. Pat. No. 5,143,854; U.S. Pat. No. 5,079,600; U.S. Pat. No. 4,923,901). Essentially, polypeptides are synthesized on a substrate (microarray) and these polypeptides can be screened with either protein molecules or fragments thereof or nucleic acid molecules in order to screen for either protein molecules or fragments thereof or nucleic acid molecules that specifically bind the target polypeptides (Fodor et al., *Science* 251: 767-773 (1991)).

It is understood that one or more of the molecules of the present invention, preferably one or more of the nucleic acid molecules or protein molecules or fragments thereof of the present invention may be utilized in a microarray based method. In a preferred embodiment of the present invention, one or more of the *D. v. virgifera* nucleic acid molecules or protein molecules or fragments thereof of the present invention may be utilized in a microarray based method. A particular preferred microarray embodiment of the present invention is a microarray comprising nucleic acid molecules encoding genes or fragments thereof that are homologues of known genes or nucleic acid molecules that comprise genes or fragments thereof that elicit only limited or no matches to known genes. A further preferred microarray embodiment of the present invention is a microarray comprising nucleic acid molecules having genes or fragments thereof that are homologues of known genes and nucleic acid molecules that comprise genes or fragment thereof that elicit only limited or no matches to known genes.

In a preferred embodiment, the microarray of the present invention comprises at least 10 nucleic acid molecules that specifically hybridize under high stringency to at least 10 nucleic acid molecules encoding *D. v. virgifera* protein or fragments thereof of the present invention. In a more preferred embodiment, the microarray of the present invention comprises at least 100 nucleic acid molecules that specifically hybridize under high stringency to at least 100 nucleic acid molecules that encode a *D. v. virgifera* protein or fragment thereof of the present invention. In an even more preferred embodiment, the microarray of the present invention comprises at least 1,000 nucleic acid molecules that specifically hybridize under high stringency to at least 1,000 nucleic acid molecules that encode a *D. v. virgifera* protein or fragment thereof of the present invention. In a further even more preferred embodiment, the microarray of the present invention comprises at least 2,500 nucleic acid molecules that specifically hybridize under high stringency to at least 2,500 nucleic acid molecules that encode a *D. v. virgifera* protein or fragment thereof of the present invention. In a preferred embodiment, at least 50%, preferably at least 70%, more preferably at least 80%, even more preferably at least 90% of the nucleic acid molecules that comprise the microarray contain one protein or fragment thereof.

Nucleic acid molecules of the present invention may be used in site directed mutagenesis. Site-directed mutagenesis may be utilized to modify nucleotide sequences, particularly as it is a technique that allows one or more of the amino acids encoded by a nucleic acid molecule to be altered (e.g. a threonine to be replaced by a methionine). Three basic methods for site-directed mutagenesis are often employed. These are cassette mutagenesis (Wells et al., *Gene* 34: 315-23 (1985)), primer extension (Gilliam et al., *Gene* 12: 129-137 (1980); Zoller and Smith, *Methods Enzymol.* 100: 468-500 (1983); Dalbadie-McFarland et al., *Proc. Natl. Acad. Sci.* (*U.S.A*). 79: 6409-6413 (1982)) and methods based upon PCR (Scharf et al., *Science* 233: 1076-1078 (1986); Higuchi et al., *Nucleic Acids Res.* 16: 7351-7367 (1988)). Site-directed mutagenesis approaches are also described in EP 0 385 962, EP 0 359 472, and PCT Patent Application WO 93/07278.

Any of the nucleic acid molecules of the present invention may either be modified by site-directed mutagenesis or used as, for example, nucleic acid molecules that are used to target other nucleic acid molecules for modification. It is understood that mutants with more than one altered nucleotide can be constructed using techniques that practitioners skilled in the art are familiar with such as isolating restriction fragments and ligating such fragments into an expression vector (see, for example, Sambrook et al., *Molecular Cloning: A Laboratory Manual*, Cold Spring Harbor Press (1989)). In a preferred embodiment of the present invention, one or more of the nucleic acid molecules or fragments thereof of the present invention may be modified by site-directed mutagenesis.

Receptors identified from the cDNA libraries of the present invention will find great use in the design of straightforward in vivo screening assays for toxins which will interact successfully with these receptors resulting in measurable effects on the cells in which the receptors reside. Briefly, suitable host cells, which contain expression vectors appropriate to the hosts for the production of the receptors of the invention displayed on the surfaces of the cells. Preferably, the host cells are eucaryotic cells such as mammalian, insect and yeast. Since the receptors are natively membrane proteins, no particular design of the expression system is required in order to effect their disposition at the cell surface. Expression vectors suitable for any desired host are generally known in the art. Procaryotic cells such as *E. coli* also may be adapted for expression of the receptor in the assay, for instance by using a reporter gene under the control of cyclic AMP and operably linked to the receptor via protein G such that toxin binding will interrupt adenyl cyclase activity and thereby produce a detectable change in reporter gene activity.

In the in vivo assays, the modified cells are contacted with the candidate toxin and the effect on metabolism or morphology is noted in the presence and absence of the candidate. The effect may be cytotoxic—i.e., the cells may themselves exhibit one of the indices of cell death, such as reduced thymidine uptake, slower increase in optical density of the culture, reduced exclusion of vital dyes (e.g., trypan blue), increased release of viability markers such as chromium and rubidium, and the like. The differential response between the toxin-treated cells and the cells absent the toxin is then noted. The strength of the toxin can be assessed by noting the strength of the response.

These assays may be conducted directly as described above or competitively with known toxins. For example, one approach might be to measure the diminution in binding of labeled BT cry toxin in the presence and absence of the toxin candidate.

In addition to simply screening candidates, the screen can be used to devise improved forms of toxins which are more specific or less specific to particular classes of insects as desired. The ability to determine binding affinity (K.sub.a and K.sub.d), dissociation and association rates, and cytotoxic effects of a candidate allows quick, accurate and reproducible screening techniques for a large number of toxins and other ligands under identical conditions which was not possible heretofore. Such information will facilitate the selection of the most effective toxins and ligands for any given receptor obtained from any desired host cell.

Competition assays may also employ RNA aptamers, peptide aptamers and antibodies that have high affinity and specificity for the receptor. The information and the structural characteristics of toxins and ligands tested will permit a rational approach to designing more efficient toxins and ligands. Additionally, such assays will lead to a better understanding of the function and the structure/function relationship of both toxin/ligand and toxin receptors on gut surface. In turn, this will allow the development of highly effective toxins/ligands.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., *Molecular Cloning: A Laboratory Manual*, Cold Spring Harbor Press (1989); Mailga et al., *Methods in Plant Molecular Biology*, Cold Spring Harbor Press (1995); Birren et al., *Genome Analysis: Analyzing DNA*, 1, Cold Spring Harbor, New York).

Having now generally described the invention, the same will be more readily understood through reference to the following examples which are provided by way of illustration, and are not intended to be limiting of the present invention, unless specified.

Example 1

Construction of the cDNA Library LIB149

The cDNA library LIB149 was generated from midguts of WCR third instar larvae. Disinfected WCR eggs were suspended in a 0.1% (w/v) agar solution and dispensed into petri dishes containing 2% (w/v) agar and filter paper. The WCR eggs were incubated first at 20° C. and 60% relative humidity for 3 days and then at 25° C. and 60% RH for 10 days. After 13 days of incubation, the eggs were washed from the dishes into sweater boxes containing soil (2 parts Metro-Mix 200:1 part Redi-Earth; steam sterilized) and germinated corn mats, which were prepared by geminating corn seeds of Pioneer varieties 3615, 3732, or CD5 in sweater boxes containing germination paper wet with 1.0% (w/v) $3336^F$ fungicide. Larvae were reared in sweater boxes in a growth chamber (25° C., 70% relative humidity, irrigated for 10 minutes every 2 days, and fertilized every 4 days). Third instar larvae were dissected to separate midguts from other body (cuticle, head, fore- and hindgut, as well as fat body). The harvested midguts were placed in chilled m.c. tube with 25 mM Tris buffer (pH 7.4), thoroughly saturated with the buffer, and then centrifuged for 5 minutes at 14,000 g at 4° C. Supernatant was discarded and midgut pellets were immediately frozen in liquid nitrogen and stored at −80° C. until total RNA preparation. RNA was purified and the cDNA library was constructed as described in Example 2.

Construction of the cDNA Library LIB150

The cDNA library LIB150 was generated from WCR pupae. Disinfected WCR eggs were suspended in a 0.1% (w/v) agar solution and dispensed into petri dishes containing 2% (w/v) agar and filter paper. The WCR eggs were incubated first at 20° C. and 60% relative humidity for 3 days and then at 25° C. and 60% RH for 10 days. After 13 days of incubation, the eggs were washed from the dishes into sweater boxes containing soil (2 parts Metro-Mix 200:1 part Redi-Earth; steam sterilized) and germinated corn mats, which were prepared by geminating corn seeds of Pioneer varieties 3615, 3732, or CD5 in sweater boxes containing germination paper wet with 1.0% (w/v) $3336^F$ fungicide. The sweater boxes containing eggs were placed in a growth chamber (25° C., 70% relative humidity, irrigated for 10 minutes every 2 days, and fertilized every 4 days) for 10 days. 10-day old larval mats were removed from the sweater boxes and transferred into an emergence box containing soil (2 parts Metro-Mix 200:1 part Redi-Earth; steam sterilized) and germinated corn lining the inside of the box. The emergence boxes were placed in a growth chamber (25° C., 70% RH, irrigated for 10 minutes every 2 days, and fertilized every 4 days) for 7 days. WCR pupae were collected, frozen in liquid nitrogen, and stored at −80° C. until total RNA preparation. RNA was purified and the cDNA library was constructed as described in Example 2.

Construction of the cDNA Library LIB3026

The cDNA library LIB3026 was generated from midguts of WCR first instar larvae. Disinfected WCR eggs were suspended in a 0.1% (w/v) agar solution and dispensed into petri dishes containing 2% (w/v) agar and filter paper. The WCR eggs were incubated first at 20° C. and 60% relative humidity for 3 days and then at 25° C. and 60% RH for 10 days. After 13 days of incubation, the eggs were washed from the dishes into sweater boxes containing soil (2 parts Metro-Mix 200:1 part Redi-Earth; steam sterilized) and germinated corn mats, which were prepared by geminating corn seeds of Pioneer varieties 3615, 3732, or CD5 in sweater boxes containing germination paper wet with 1.0% (w/v) 3336$^F$ fungicide. Larvae were reared in sweater boxes in a growth chamber (25° C., 70% relative humidity, irrigated for 10 minutes every 2 days, and fertilized every 4 days). First instar larva were dissected to separate midguts from other body (cuticle, head, fore- and hindgut, as well as fat body). The harvested midguts are placed in chilled m.c. tube with 25 mM Tris buffer (pH 7.4), thoroughly saturated with the buffer, and then centrifuged for 5 minutes at 14,000 g at 4° C. Supernatant was discarded and midgut pellets were immediately frozen in liquid nitrogen and stored at −80° C. until total RNA preparation. RNA was purified and the cDNA library was constructed as described in Example 2.

Construction of the cDNA Library LIB3373

The cDNA library LIB3373 was generated from whole guts of WCR third instar larvae. Western corn rootworm eggs were prepared weekly. Eggs were separated from soil by floating in a separatory funnel containing a 1.25 specific gravity solution of magnesium sulfate. Once separated, the eggs were surface disinfected in 0.25% peroxyacetic acid, rinsed, treated with Nystatin (2 mg/ml), and plated onto sterile filter disks on 2% agar. Egg plates were incubated at 25° C. for two weeks then transferred to corn seedling boxes (described below).

Corn seedlings for rearing the hatching larvae were prepared weekly by treating approximately 1 kg of corn seeds with 25% bleach for five minutes, followed by rinsing. Corn seed was divided into twelve sterile tissue culture boxes, each containing germination paper and 200 ml of 1% Domain fungicide solution. Germination temperature was 29° C. and germinating seedlings were ready for infestation one week after preparation. Following infestation, rearing boxes were incubated at 25° C.

Third instar larvae were harvested from the seedling boxes eight to twelve days following infestation. Insects were harvested by placing infested corn mats onto a screen within a large funnel (60 cm). As insects crawled out of the root mass, they would fall through the funnel into a 50 ml screwcap tube (on ice).

Third instar larva were dissected to separate guts from other body (cuticle, head, and fat body). The harvested guts were placed in chilled m.c. tube with 25 mM Tris buffer (pH 7.4), thoroughly saturated with the buffer, and then centrifuged for 5 minutes at 14,000 g at 4° C. Supernatant was discarded and gut pellets were immediately frozen in liquid nitrogen and stored at −80° C. until total RNA preparation.

Total RNA was isolated using the Pharmacia QuickPrep Total RNA Extraction Kit, following the protocol recommended by the manufacturer. Poly A+ RNA (mRNA) was purified using QuickPrep kit from Amersham Pharmacia Biotech, Inc. (Piscataway, N.J.), essentially as recommended by the manufacturer.

Construction of cDNA libraries is well-known in the art and a number of cloning strategies exist. A number of cDNA library construction kits are commercially available. The Stratagene cDNA Synthesis Kit (Stratagene, La Jolla, Calif.) was used, following the conditions suggested by the manufacturer. The cDNA was ligated into a Lambda Zap vector.

Example 2

Total RNA was purified using Trizol reagent from Life Technologies (Gibco BRL, Life Technologies, Gaithersburg, Md. U.S.A.), essentially as recommended by the manufacturer. Poly A+ RNA (mRNA) was purified using magnetic oligo dT beads essentially as recommended by the manufacturer (Dynabeads, Dynal Corporation, Lake Success, N.Y. U.S.A.).

Construction of cDNA libraries is well-known in the art and a number of cloning strategies exist. A number of cDNA library construction kits are commercially available. The Superscript™ Plasmid System for cDNA synthesis and Plasmid Cloning (Gibco BRL, Life Technologies, Gaithersburg, Md. U.S.A.) was used, following the conditions suggested by the manufacturer. The cDNA was ligated into pSPORT cloning vector.

Example 3

The cDNA libraries were plated on LB agar containing the appropriate antibiotics for selection and incubated at 37° for a sufficient time to allow the growth of individual colonies. Single colonies were individually transferred to each well of 96-well microtiter plates containing LB liquid including selective antibiotics. The plates were incubated overnight at approximately 37° C. with gentle shaking to promote growth of the cultures. The plasmid DNA was isolated from each clone using Qiaprep plasmid isolation kits, using the conditions recommended by the manufacturer (Qiagen Inc., Santa Clara, Calif. U.S.A.).

The template plasmid DNA clones were used for subsequent sequencing. For sequencing the cDNA libraries LIB149, LIB150, and LIB3026, a commercially available sequencing kit, such as the ABI PRISM dRhodamine Terminator Cycle Sequencing Ready Reaction Kit with AmpliTaq® DNA Polymerase, FS, was used under the conditions recommended by the manufacturer (PE Applied Biosystems, Foster City, Calif.). The ESTs of the present invention were generated by sequencing initiated from the 5' end of each cDNA clone.

A number of sequencing techniques are known in the art, including fluorescence-based sequencing methodologies. These methods have the detection, automation and instrumentation capability necessary for the analysis of large volumes of sequence data. Currently, the 377 DNA Sequencer (Perkin-Elmer Corp., Applied Biosystems Div., Foster City, Calif.) allows the most rapid electrophoresis and data collection. With these types of automated systems, fluorescent dye-labeled sequence reaction products are detected and data entered directly into the computer, producing a chromatogram that is subsequently viewed, stored, and analyzed using the corresponding software programs. These methods are known to those of skill in the art and have been described and reviewed (Birren et al., *Genome Analysis: Analyzing DNA*, 1, Cold Spring Harbor, N.Y., the entirety of which is herein incorporated by reference).

Example 4

Sequencing of the cDNA library LIB3373 was carried out using the primary library as the source for sequencing template. Two methods were used to isolate sequencing template: phagemid excision and single phage PCR.

In the phagemid excision method, 400-800 plaques are spread evenly over a bacterial lawn on multiple Petri plates. Blue/white selection was performed to identify putative phage containing gut inserts. White plaques were individually isolated and stored at 4° C. These are stable for several months, and thus can be isolated less frequently in greater numbers (e.g., once a month). Phagemid excision was performed in 96-sample sets from the phage stocks. This step releases the plasmid vector (containing the cDNA insert)

from the Uni-Zap phage vector. This protocol was modified from Stratagene's protocol to facilitate phage adhesion and growth in 96-well culture blocks (~1.45 ml volumes). Plaques were allowed to adhere to and multiply in XL1 Blue cells co-infected with Helper phage. Cell lysis releases filamentous phage which is used to infect SOLR cells, where phagemid excision takes place. After excision, cells containing phagemids with insert were identified by a second round of selection (ampicillin resistance, blue/white colonies) immediately before isolation of DNA. Sequence-quality DNA was isolated using the Qiagen TurboPrep protocol (96-well format) and screened (EcoRI×XhoI digest) for the presence and approximate size of insert before setting up template/primer reactions. DNA sequences were then analyzed for ambiguous sequence and vector contamination and trimmed using a commercially available computer software (Sequencher), and submitted as gapped BLAST searches for comparison to public nucleotide and protein databases.

The other method utilized PCR to amplify individual inserts directly from phage; this was performed without isolation of phage DNA. The PCR reaction was carried out in 96-well format using the M13 Reverse and −20 primers. A portion of the PCR product was analyzed on an agarose gel to determine presence and size of insert. The remainder of the PCR product was purified using Qiagen's PCR Purification kit. Sequencing was then conducted using nested primers (T3/T7). This method involves a number of steps that are analogous to the excision screening method (phage isolation, DNA purification, digest/PCR setup, agarose electrophoresis, sequence set-up) and is nearly as labor-intensive. However, this method has the potential to increase the number of clones that can be screened per week because plating is not necessary. All completed sequences were trimmed for vector contamination and ambiguous regions.

Example 5

This example illustrates sequence comparison to determine the similarity/identity of the test or query sequence with sequences in publicly available or proprietary databases. A characteristic feature of a protein or DNA sequence is that it can be compared with other known protein or DNA sequences. Sequence comparisons can be undertaken by determining the similarity of the test or query sequence with sequences in publicly available or proprietary databases ("similarity analysis") or by searching for certain motifs ("intrinsic sequence analysis") (e.g. cis elements) (Coulson, *Trends in Biotechnology,* 12: 76-80 (1994); Birren, et al., *Genome Analysis,* 1: 543-559 (1997); both of which are herein incorporated by reference in their entirety).

Similarity analysis includes database search and alignment. Examples of public databases include the DNA Database of Japan (DDBJ); Genebank; and the European Molecular Biology Laboratory Nucleotide sequence Database (EMBL).

A number of different search algorithms have been developed, one example of which are the suite of programs referred to as BLAST programs. There are five implementations of BLAST, three designed for nucleotide sequences queries (BLASTN, BLASTX, and TBLASTX) and two designed for protein sequence queries (BLASTP and TBLASTN) (Coulson, *Trends in Biotechnology,* 12: 76-80 (1994); Birren, et al., *Genome Analysis,* 1: 543-559 (1997)).

BLASTN takes a nucleotide sequence (the query sequence) and its reverse complement and searches them against a nucleotide sequence database. BLASTN was designed for speed, not maximum sensitivity, and may not find distantly related coding sequences. BLASTX takes a nucleotide sequence, translates it in three forward reading frames and three reverse complement reading frames, and then compares the six translations against a protein sequence database. BLASTX is useful for sensitive analysis of preliminary (single-pass) sequence data and is tolerant of sequencing errors (Gish and States, *Nature Genetics,* 3: 266-272 (1993), herein incorporated by reference). BLASTN and BLASTX may be used in concert for analyzing EST data (Coulson, *Trends in Biotechnology,* 12: 76-80 (1994); Birren et al., *Genome Analysis,* 1: 543-559 (1997)).

Given a coding nucleotide sequence and the protein it encodes, it is often preferable to use the protein as the query sequence to search a database because of the greatly increased sensitivity to detect more subtle relationships. This is due to the larger alphabet of proteins (20 amino acids) compared with the alphabet of nucleotide sequences (4 bases), where it is far easier to obtain a match by chance. In addition, with nucleotide alignments, only a match (positive score) or a mismatch (negative score) is obtained, but with proteins, the presence of conservative amino acid substitutions can be taken into account. Here, a mismatch may yield a positive score if the non-identical residue has physical/chemical properties similar to the one it replaced. Various scoring matrices are used to supply the substitution scores of all possible amino acid pairs. A general purpose scoring system is the BLOSUM62 matrix (Henikoff and Henikoff, *Proteins,* 17: 49-61 (1993), herein incorporated by reference in its entirety), which is currently the default choice for BLAST programs. BLOSUM62 is tailored for alignments of moderately diverged sequences and thus may not yield the best results under all conditions. Altschul, *J. Mol. Biol.* 36: 290-300 (1993), herein incorporated by reference in its entirety, uses a combination of three matrices to cover all contingencies. This may improve sensitivity, but at the expense of slower searches. In practice, a single BLOSUM62 matrix is often used but others (PAM40 and PAM250) may be attempted when additional analysis is necessary. Low PAM matrices are directed at detecting very strong but localized sequence similarities, whereas high PAM matrices are directed at detecting long but weak alignments between very distantly related sequences.

Homologues in other organisms are available that can be used for comparative sequence analysis. Multiple alignments are performed to study similarities and differences in a group of related sequences. CLUSTAL W is a multiple sequence alignment package available that performs progressive multiple sequence alignments based on the method of Feng and Doolittle, *J. Mol. Evol.* 25: 351-360 (1987), the entirety of which is herein incorporated by reference. Each pair of sequences is aligned and the distance between each pair is calculated; from this distance matrix, a guide tree is calculated, and all of the sequences are progressively aligned based on this tree. A feature of the program is its sensitivity to the effect of gaps on the alignment; gap penalties are varied to encourage the insertion of gaps in probable loop regions instead of in the middle of structured regions. Users can specify gap penalties, choose between a number of scoring matrices; or supply their own scoring matrix for both the pairwise alignments and the multiple alignments. CLUSTAL W for UNIX and VMS systems is available at: ftp.ebi.ac.uk. Another program is MACAW (Schuler et al., *Proteins, Struct. Func. Genet,* 9:180-190 (1991), the entirety of which is herein incorporated by reference, for which both Macintosh and Microsoft Windows versions are available. MACAW uses a graphical interface, provides a choice of several alignment algorithms, and is available by anonymous ftp at: ncbi.nlm.nih.gov (directory/pub/macaw).

Sequence motifs are derived from multiple alignments and can be used to examine individual sequences or an entire database for subtle patterns. With motifs, it is sometimes possible to detect distant relationships that may not be demonstrable based on comparisons of primary sequences alone. Currently, the largest collection of sequence motifs in the world is PROSITE (Bairoch and Bucher, *Nucleic Acid Research,* 22: 3583-3589 (1994), the entirety of which is herein incorporated by reference.) PROSITE may be accessed via either the ExPASy server on the World Wide Web or anonymous ftp site. Many commercial sequence analysis packages also provide search programs that use PROSITE data.

A resource for searching protein motifs is the BLOCKS E-mail server developed by S. Henikoff, *Trends Biochem Sci.,* 18:267-268 (1993); Henikoff and Henikoff, *Nucleic Acid Research,* 19:6565-6572 (1991); Henikoff and Henikoff, *Proteins,* 17: 49-61 (1993); all of which are herein incorporated by reference in their entirety). BLOCKS searches a protein or nucleotide sequence against a database of protein motifs or "blocks." Blocks are defined as short, ungapped multiple alignments that represent highly conserved protein patterns. The blocks themselves are derived from entries in PROSITE as well as other sources. Either a protein or nucleotide query can be submitted to the BLOCKS server; if a nucleotide sequence is submitted, the sequence is translated in all six reading frames and motifs are sought in these conceptual translations. Once the search is completed, the server will return a ranked list of significant matches, along with an alignment of the query sequence to the matched BLOCKS entries.

Conserved protein domains can be represented by two-dimensional matrices, which measure either the frequency or probability of the occurrences of each amino acid residue and deletions or insertions in each position of the domain. This type of model, when used to search against protein databases, is sensitive and usually yields more accurate results than simple motif searches. Two popular implementations of this approach are profile searches (such as GCG program ProfileSearch) and Hidden Markov Models (HMMs) (Krough et al., *J. Mol. Biol.* 235:1501-1531 (1994); Eddy, *Current Opinion in Structural Biology* 6:361-365 (1996), both of which are herein incorporated by reference in their entirety). In both cases, a large number of common protein domains have been converted into profiles, as present in the PROSITE library, or HHM models, as in the Pfam protein domain library (Sonnhammer et al., *Proteins* 28:405-420 (1997), the entirety of which is herein incorporated by reference). Pfam contains more than 500 HMM models for enzymes, transcription factors, signal transduction molecules, and structural proteins. Protein databases can be queried with these profiles or HMM models, which will identify proteins containing the domain of interest. For example, HMMSW or HMMFS, two programs in a public domain package called HMMER (Sonnhammer et al., *Proteins* 28:405-420 (1997)) can be used.

PROSITE and BLOCKS represent collected families of protein motifs. Thus, searching these databases entails submitting a single sequence to determine whether or not that sequence is similar to the members of an established family. Programs working in the opposite direction compare a collection of sequences with individual entries in the protein databases. An example of such a program is the Motif Search Tool, or MoST (Tatusov et al. *Proc. Natl. Acad. Sci.* 91: 12091-12095 (1994), the entirety of which is herein incorporated by reference.) On the basis of an aligned set of input sequences, a weight matrix is calculated by using one of four methods (selected by the user); a weight matrix is simply a representation, position by position in an alignment, of how likely a particular amino acid will appear. The calculated weight matrix is then used to search the databases. To increase sensitivity, newly found sequences are added to the original data set, the weight matrix is recalculated, and the search is performed again. This procedure continues until no new sequences are found.

Table 1 lists the nucleic acid molecules encoding homologs of known proteins.

Lengthy table referenced here

US08614370-20131224-T00001

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US08614370B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08614370B2). An electronic copy of the "Sequence Listing" will also be available from the USPTO upon request and payment of the fee set forth in 37 CFR 1.19(b)(3).

What is claimed is:

1. A nucleic acid molecule complementary to at least 20 contiguous nucleotides of a sequence selected from the group consisting of SEQ ID NO: 2491 and SEQ ID NO: 2492, wherein an antisense RNA expressed from said nucleic acid molecule reduces the expression of a *D. v. virgifera* gene comprising said SEQ ID NO: 2491 or SEQ ID NO: 2492, and wherein the nucleic acid molecule is operably linked to a heterologous promoter that causes transcription of DNA in plant cells.

2. The nucleic acid molecule of claim 1, wherein the nucleic acid molecule is complementary to part of SEQ ID NO:2491.

3. The nucleic acid molecule of claim 2, wherein the nucleic acid molecule is complementary to all of SEQ ID NO:2491.

4. The nucleic acid molecule of claim 1, wherein the nucleic acid molecule is complementary to part of SEQ ID NO:2492.

5. The nucleic acid molecule of claim 4, wherein the nucleic acid molecule is complementary to all of SEQ ID NO:2492.

6. The nucleic acid molecule of claim 1, wherein the nucleic acid molecule comprises a fragment of from about 20 to 20 to about 250 nucleotides complementary to the sequence of SEQ ID NO:2491.

7. The nucleic acid molecule of claim 1, wherein the nucleic acid molecule comprises a fragment of from about 20 to 20 to about 250 nucleotides complementary to the sequence of SEQ ID NO:2492.

8. A construct comprising the nucleic acid molecule of claim 1.

9. A transgenic plant comprising the nucleic acid molecule of claim 1.

10. The transgenic plant of claim 9, which is a corn plant.

11. A cell comprising the nucleic acid molecule of claim 1.

12. The cell of claim 11, wherein the cell is an *Agrobacterium* sp., *E. coli* or a plant cell.

13. The cell of claim 12, wherein the cell is a plant cell.

14. The cell of claim 13, wherein the cell is a corn plant cell.

* * * * *

UNITED STATES PATENT AND TRADEMARK OFFICE
CERTIFICATE OF CORRECTION

Page 1 of 1

PATENT NO. : 8,614,370 B2
APPLICATION NO. : 12/606948
DATED : December 24, 2013
INVENTOR(S) : Scott E. Andersen et al.

It is certified that error appears in the above-identified patent and that said Letters Patent is hereby corrected as shown below:

In the Claims

Column 56, Line 2, Claim 6, please delete "about 20 to 20 to about 250", and insert --20 to about 250--

Column 56, Line 6, Claim 7, please delete "about 20 to 20 to about 250", and insert --20 to about 250--

Signed and Sealed this
Eighteenth Day of March, 2014

Michelle K. Lee
*Deputy Director of the United States Patent and Trademark Office*